US007899624B2

(12) United States Patent
Cualing et al.

(10) Patent No.: US 7,899,624 B2
(45) Date of Patent: Mar. 1, 2011

(54) VIRTUAL FLOW CYTOMETRY ON IMMUNOSTAINED TISSUE-TISSUE CYTOMETER

(76) Inventors: Hernani Del Mundo Cualing, Lutz, FL (US); Eric Zhong, East Brunswick, NJ (US)

(*) Notice: Subject to any disclaimer, the term of this patent is extended or adjusted under 35 U.S.C. 154(b) by 1031 days.

(21) Appl. No.: 11/492,167

(22) Filed: Jul. 25, 2006

(65) Prior Publication Data
US 2007/0020697 A1 Jan. 25, 2007

Related U.S. Application Data

(60) Provisional application No. 60/701,774, filed on Jul. 25, 2005.

(51) Int. Cl.
*G06F 19/00* (2006.01)
*G06K 9/52* (2006.01)
(52) U.S. Cl. .......................................... 702/19; 382/133
(58) Field of Classification Search ........................ None
See application file for complete search history.

(56) References Cited

U.S. PATENT DOCUMENTS 5,732,150 A * 3/1998 Zhou et al. .................. 382/133
6,151,405 A * 11/2000 Douglass et al. ............. 382/133

OTHER PUBLICATIONS

Ong et al. Image Analysis of Tissue Sections Comput. Biol Med. vol. 26, pp. 269-279 (1996).*
Steiner et al. Automated data acquisition by confocal laser scanning microscopy and image analysis of triple stained immunofluorescent leukocytes in tissue. Journal of Immunological Methods vol. 237, pp. 39-50 (2000).*
Dow et al. Automatic Multiparameter Fluorescence Imaging for Determining Lymphocyte Phenotype and Activation Status in Melanoma Tissue Sections Cytometry vol. 25, pp. 71-81 (1996).*
Ranefall et al. Automatic quantification of immunohistochemically stained cell nuclei based on standard reference cells. Analytical Cellular Pathology vol. 17 pp. 111-123 (1998).*

* cited by examiner

*Primary Examiner* — John S Brusca
(74) *Attorney, Agent, or Firm* — Hernani Cualing; IHCFLOW, Inc.

(57) ABSTRACT

An automated method for rapidly analyzing percentage of positive cells from immunostained tissue sections is disclosed. The method is an improved multi-stage dynamic thresholding series of steps applied to monochromatic grayscale values of color channels of digital image of tissue. The method requires color digital images of tissue. The method discloses sequential stages to obtain a step-wise progression of preliminary image planes iteratively combined to obtain a final immunostained and non-immunostained images of cells of the same cell class. The final results are segmented cells that are digitally countable. The percent of immunostained cells over the total cells are calculated in tissue section. The cell characteristics, including cell size and its immunostaining intensity are captured and digitally stored per cell. The segmented single cell color image as well as the corresponding cell characteristic are displayed as a dot plot two-dimensional flow cytometry-like manner.

3 Claims, 11 Drawing Sheets
(7 of 11 Drawing Sheet(s) Filed in Color)

NUMERATOR

DENOMINATOR

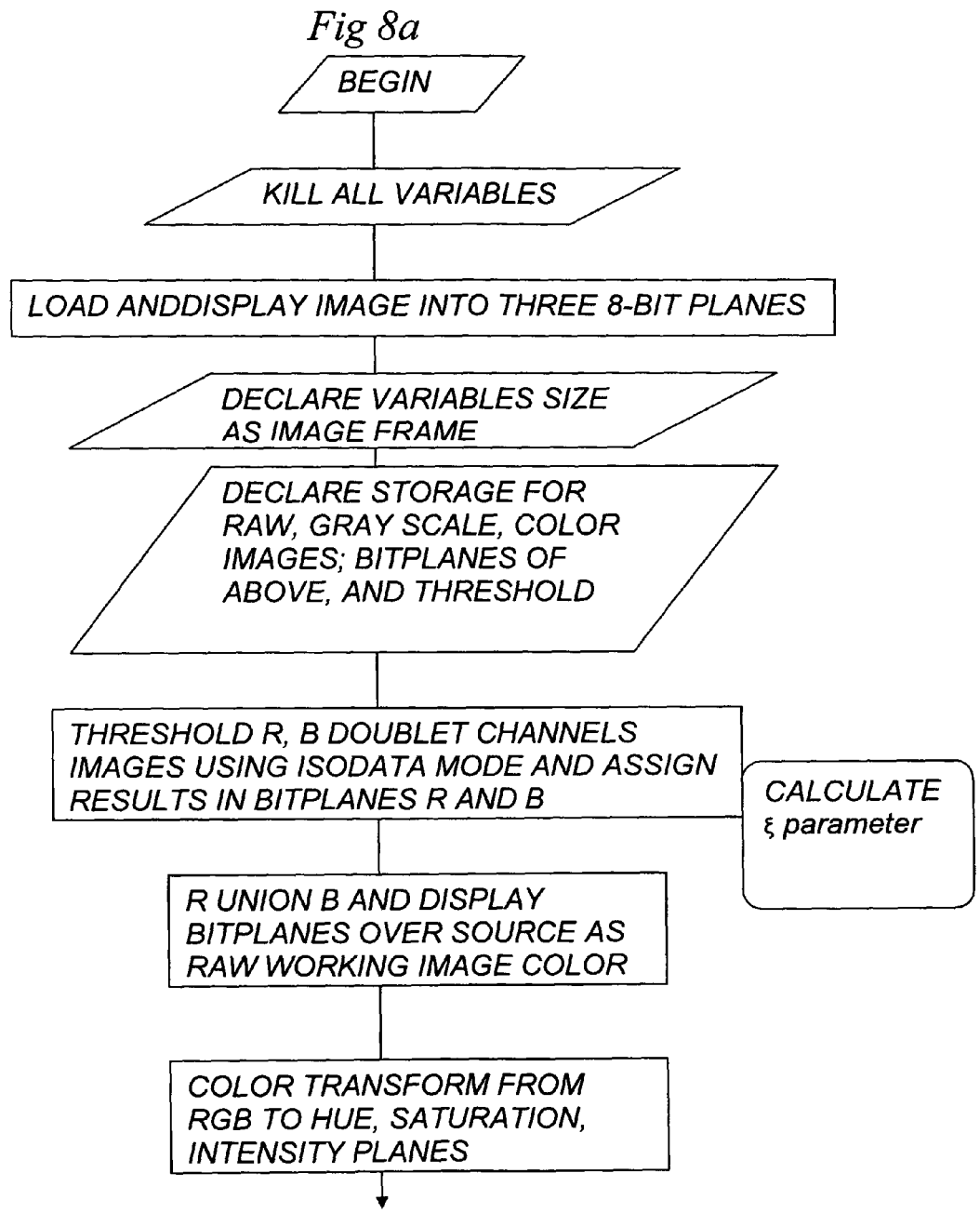

FIG. 8-B
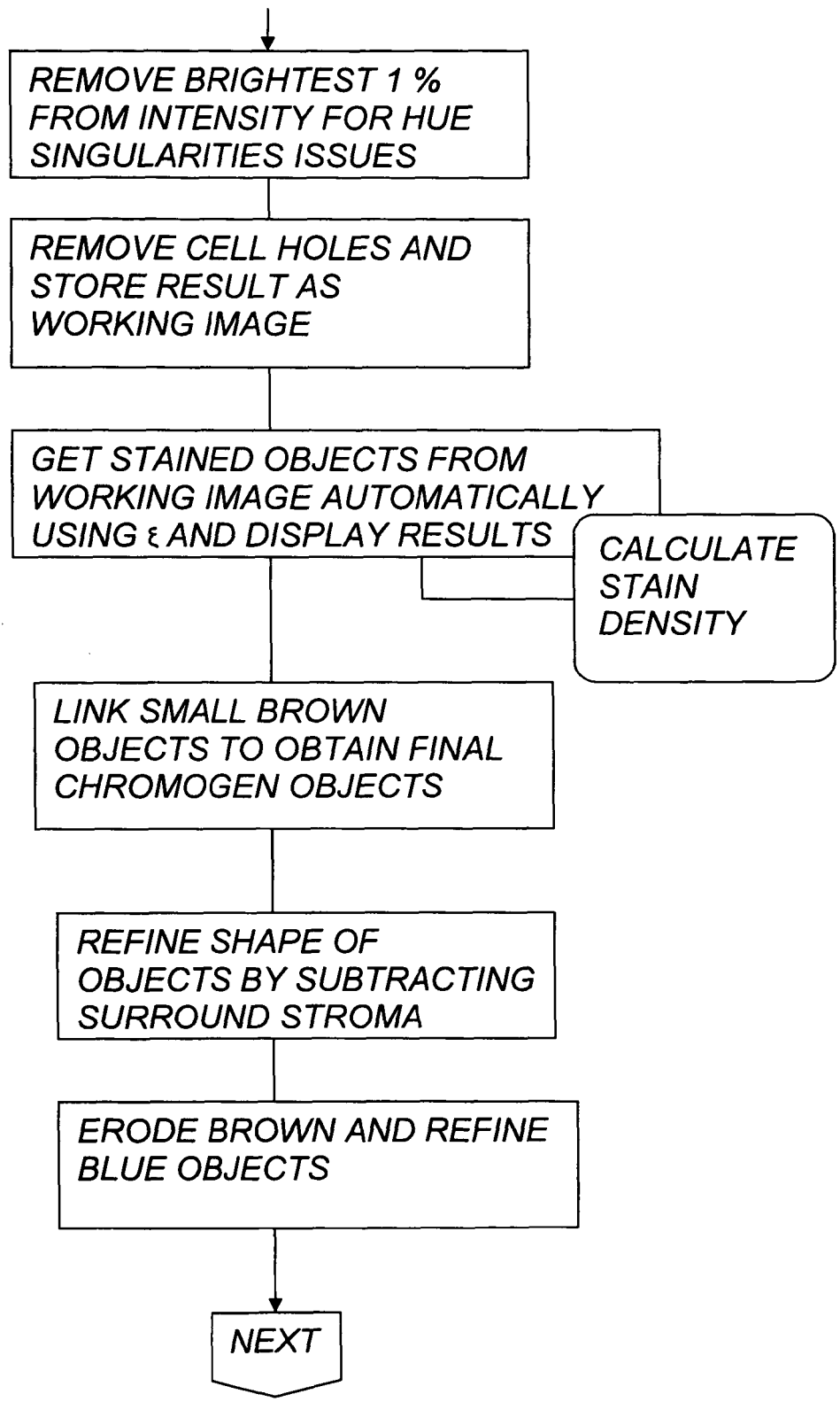

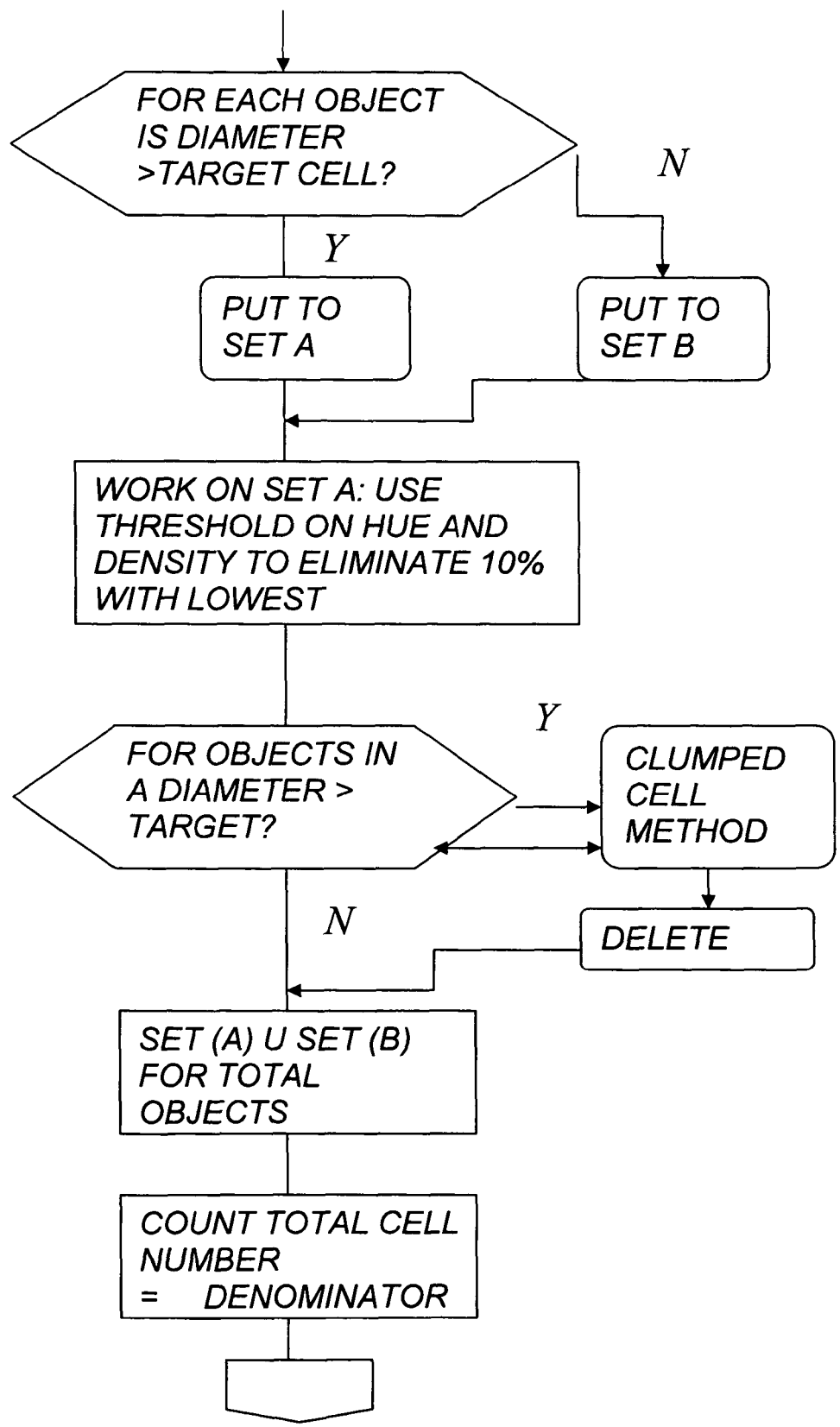
FIG. 8-C

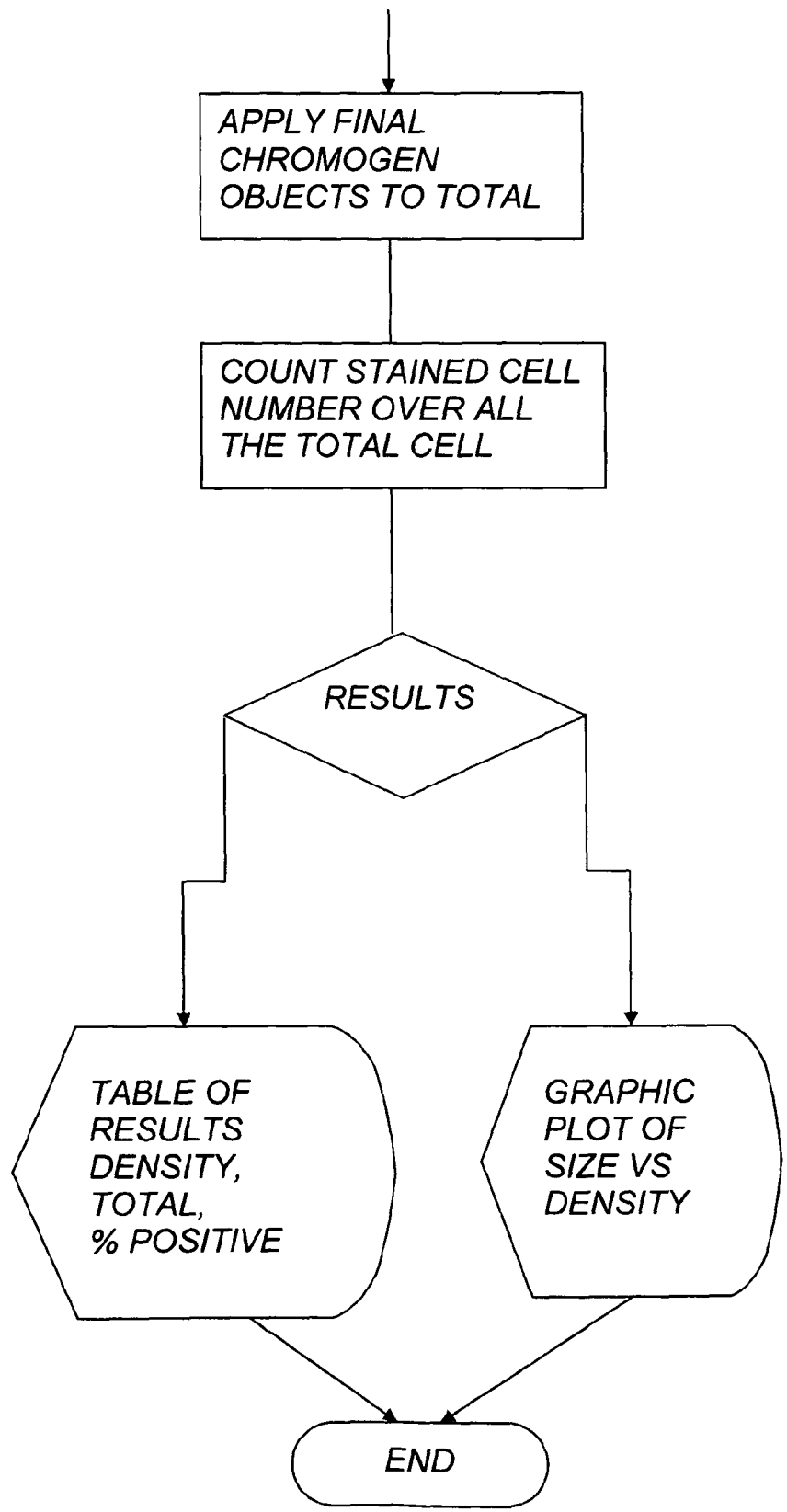

VIRTUAL FLOW CYTOMETRY ON IMMUNOSTAINED TISSUE-TISSUE CYTOMETER

CROSS REFERENCE TO RELATED APPLICATIONS

Claim of Priority

This application claims the benefit of priority, under 35 USC .sctn.119(e)(1), of provisional application No. 60/701,774, filed Jul. 25, 2005. The entirety of that provisional application is incorporated herein by reference.

FEDERALLY SPONSORED RESEARCH

Not applicable.

REFERENCE TO A COMPUTER FLOW CHART

Program flow chart in the drawings

TECHNICAL FIELD

The invention relates generally to a system for automated light microscopic image analysis, specifically to computerized methods of converting immunohistochemistry color image to objective, clinically useful, statistical single cell data now commonly associated with flow cytometry—but herein performed on paraffin embedded tissue sections.

BACKGROUND OF INVENTION

1. Introduction

The optical microscope in the diagnostic and biomedical laboratory is routinely used by pathologists and research scientist to make diagnosis and perform experiments. These users perform these functions by visualizing cells and tissue sections that have been previously prepared and chemically stained in the histology or histochemistry laboratory. Every patient with a tumor suspected of cancer undergoes evaluation with the most critical pathway involving a tissue biopsy. The biopsy tissue is routinely fixed in formalin, processed in a tissue processor, embedded in formalin and serially cut in a microtome to give thin sections representing the diagnostic material. The diagnostic material then is a representative tissue section with tangentially cut whole cells and chemically marked with mordant dyes and indicia markers. One of the ubiquitous dyes is the nuclear counter stain hematoxylin and one of the common indicia markers are the monoclonal antibody or nuclear acid probes tagged with an enzyme reagent and a chromogenic substrate. The most common chromogenic substrate is DAB (diaminobenzidine) which is visualized as reddish brown and the most common nuclear counter stain is hematoxylin which is visualized as blue.

The diagnosis is performed by examining the tissue optically using the objective lenses of the microscope in low and high power magnifications. The routinely stained hematoxylin and eosin tissue is examined first to visualize the presence of tumor or benign cells and in the majority of cases, confirmed by a panel or set of immunohistochemical stains targeting lineage, proliferative, tumor associated or prognostic or oncogenic markers. The current state of the art of diagnosis is to estimate the percentage of immunohistochemically stained cells and based on this subjective interpretation render a diagnosis. No tool is currently available to use computerized image analysis to count and display these relevant cells for the pathologist or scientist. Counting and identifying these cells are crucial in making decisions for diagnosis or prognosis, yet the diagnostic practice relies on a subjective approach, even though patient outcomes and treatment decisions are at stake.

The latter practice is the standard of practice, not because it is the optimal way, but because of an absence of an automated cell-quantifying instrument attached to the microscope. This practice is subjective, error prone, and often gives wide range of results that depends on the level of microscopist's skill. This is due to difficulty in counting positive cells accurately because of overlapped stained nuclei, variability of staining, and the limitation of our visual system.

To analyze immunostained cells, we have two major techniques: flow cytometry and immunohistochemistry. On one hand, the flow cytometer, requires a viable tissue disaggregated to individual live cells to quantify the cells. These viable cells are identified using fluorescent-tagged antibody probes in a highly accurate way, but will not allow concurrent visualization of the cells analyzed. Immunohistochemistry, on the other hand, uses formalin-fixed non-viable tissue specimen and chromogen-tagged antibodies of defined specificity to identify, mark, and concurrently visualize specific types of cells, the latter function not present in flow cytometry. There is desire and need for the pathologists to both quantify and see tissues to have valid, real time, objective feedback on the types and cells identified to make the crucial diagnosis or prognosis.

However, there is currently no system that will perform "flow cytometry" to identify the types and the percentage of the immunostained cells in fixed tissue. Using our novel proposed technology, we combine the advantages provided by flow cytometry in quantifying cells and also retain the advantages of microscopy in morphologically visualizing the immunoreactive cells. To accomplish this aim, we resort to new and improved advance image analysis using a surprisingly easy and unique, useful, novel process as described herein.

Immunohistochemistry (IHC) is indispensable in clinical practice yet a tool to count cells in a novel intuitive way is not available and is needed. The current state of the clinical art in pathology diagnosis allows the pathologists to either make a judgment call for a positive or negative result of immunohistochemistry or semi quantitatively grade the percentage of relevant positive or negative population and give a percentage estimate based on the pathologist subjective feel of the extent of positive reaction. Routinely in pathology practice, a panel of 5 to 15 immunohistochemistry antibodies are applied on the slide-based tissue sections to create a differential matrix to rule in or out a diagnosis based on the tumor associated markers. Most of diagnostic pathology, whether a small office or a large reference laboratory, uses immunohistochemistry as part of a standard of practice. In practice, the use of IHC may shift the diagnostic probability, for example from 75% to 100%. This is especially true in hematopathology diagnosis where an enhanced diagnostic accuracy is reported if the immunologic results are included (Blood, Armitage et al., Int Lymphoma Study Group, 1997). The enhanced accuracy is reported to an increased accuracy beyond the routine hematoxylin and eosin stained tumor from 5 to 35% of the cases.

Current image analysis in diagnostic centers are specialized tools to semiquantitate hormone receptor antigen for prognosis only. Yet none of these diagnostic centers have an automated method with which to count cells in immunohistochemistry stained slides in other tumor types or even in cancers of the lymphatics such as lymphomas. Automated detection of chromogen stained biological cells in tissue in a population statistic manner has lagged behind quantitation of antigen in tissue and cells for prognosis and diagnosis, i.e., Her2neu, ER, PR hormones profile for breast cancer.

Current image analysis approaches and those systems describe above are inadequate to perform a "virtual flow cytometry" on tissue. Many of the tissues submitted for diagnosis are fixed in formalin and subjected to immunohistochemistry to aid or confirm the diagnosis. In immunohistochemically stained cells in tissue, the cells are often ambiguously and syncitially linked, variable in size, variable in intensity staining, variable in color staining, with much overlap that even expert guided manual counting is difficult to be accurate. Despite these obvious difficulties, the percentage of positive staining cells is currently estimated visually by eye without the aid of a computerized tool. The level of accuracy of expert observers varies by as much as 25%. The goal then is to exceed this performance using rapid and robust computerized automation.

Current image analysis techniques perform image analysis based on chromogen associated pixel comparison using a dedicated instrument with transmitted light operation set within a narrow range. The problem with this prevailing approach is that the chromogen associated pixels often are associated with the pixels with the counter stain dyes. A cell has a nucleus, a cytoplasm and a surface cell membrane. Membrane reactive brown chromogen bleeds into the cytoplasm and include most of the nuclear area as well (FIG. 3, color frame 14 and FIG. 4a in drawings). These color mixture makes it difficult to isolate the brown only pixels and simple detection of antigen density by looking for brown pixels will not be able to easily extract the brown chromogen apart from the blue dye. Moreover, the staining variability and tumor antigen expression variability may increase or decrease color intensity of these chromogen. This variability is not so easily correlated with pixel distribution. The staining variability is also related to the level of transmitted light. By limiting this variable, a pathologist who often obtain images from microscope with little regard for a set light but based on comfort of vision, often extract images in random light intensity. The prior art limitation by being a dedicated machine with set lighting precludes routine use in diagnostic pathology and evaluation of immunohistochemistry in a routine manner.

Because these approaches do not detect single cells of the same type or class, no single cell percentage could be obtained. The usual result is percent of pixels overall the area examined. These areas are often called hot spots to indicate an approximate location of relevant cells.

Segmentation of biological images of chromogen-marked microscopic cellular images is difficult because of the variability of these images. Color in immunostained cells in tissue varies from strongly stained to weakly stained cells. The chromogens used may also vary. Furthermore, color segmentation tools are not readily available or easily applied. RGB (Red Green Blue) by itself, its various expressions and combinations as used in many current systems and approaches, are tightly linked with intensity component and therefore, any ratio derived from them will be biased by the black and white components of the image. True color image analysis is not achievable. Therefore, these algorithms rely on grayscale-discriminating segmentation paradigms which are incapable of solving problems of variability in staining, or the identification of nuclei of unstained and stained cells, and cells stained with different color of chromogens (tissue stain). The difficulty lies in the inability of these paradigms to separate intensity from chromatic properties of tissue stains.

There is still a need to bridge the perception prevalent in literature on microscopic images and the low-level image features that most algorithm are based on. Current algorithms try to find the best technique to solve technical problems on limited data sets addressing solution to historical problems by solving to the level of the primitives and comparing results with other approaches. One difficulty of this approach in the real world problems in biological detection is complex and that most often, it is the combination of techniques and the empirical adaptive human responses to the results that point to the acceptable solutions. The ground truth in most biological images in the domain of automated immunohistochemistry may be fuzzy, ill defined and subjective. Therefore, it is not so much as the accuracy of thresholding the exact boundaries of individual object that may be relevant but it is as much as the relevance of enumerating the individual objects of the population being studied. It is like the problem of hitting the bull but not necessarily the bull's eye. It also follows that the approach to solve this generic problem is not to develop low-level feature detection algorithms but on the development of a combination of low-level features detection tempered by the feedback from human observers.

2. Prior Art

U.S. Pat. No. 6,692,952 Feb. 17, 2004 Braff, R. MIT

This invention relates to cell analysis and sorting devices and methods for manipulating single cells using these microscopic devices. The devices use cells in fluidics similar to flow cytometry and does not use routine stained slides by immunohistochemistry means.

U.S. Pat. No. 6,294,331 Sep. 25, 2001 Ried, T. USA

This invention relates to methods of detecting genetic and phenotypic markers in biological samples on slides using spectral imaging and brightfield microscopy to detect the presence of chromogenic dyes. The analysis is not single cell and will not perform percentage of the same class of cells.

U.S. Pat. No. 6,215,892 2001-2004 Douglass, J. Chromavision

The present invention has utility in the field of oncology for the early detection of minimal residual disease ("micro metastases") on microscopic slides but does not seek or report the percentage of single cells.

U.S. Pat. No. 6,418,236 2002-2007 Ellis, B. Chromavision

The invention relates generally to light microscopy and, more particularly, to automated techniques of analyzing cytochemical and immunohistochemical staining on slides. The method and results, though based on color ratios of RGB, are not based on single cell analysis of same class of cells and will not present results in a two dimensional histogram.

U.S. Pat. No. 6,404,916 Jun. 11,2002 De La Torre-Bueno, J. Chromavision

This invention deals with an apparatus of digital components to perform color threshold analysis by volume distribution. The subject is locally adaptable in machine vision field and may not be useful in detecting immunostained cells in tissue, wherein these cells are in a contiguous distribution with a gradation and mixture of bleeding colors, as is often the situation with immunohistochemical stains of cells using brown chromogen and blue counterstain. The periphery of the cell is brown and the center is blue precluding use of a color analyzer predicated on homogeneous color volumes. This invention takes teaching from one well known classical method that converts the RGB color information into another color space, such as HSI (hue, saturation, intensity) space (1) Two book references by Russ J C, and (2) Gonzales R C addressed this issue in detail. In such a space, distinctly different hues such as red, blue, green, yellow, may be readily separated. In addition, relatively lightly stained objects may be distinguished from more intensely stained ones by virtue of differing saturations. Converting from RGB space to HSI space requires more complex computation not necessarily needing a dedicated hardware as this invention is about, but is within the real time span methods of the current image processors and personal computers with fast central processors.

U.S. Pat. No. 6,337,472 Jan. 8, 2002 Garner, H. Univ. of Texas

The present invention relates in general to the field of biological sample analysis, and more particularly, to an apparatus and method for observing, identifying and quantifying a biological sample through a microscope using the entire spectrum of light, concurrently and in real time. There is not single cell identification but the invention is predicated on pixel distribution of detected moieties.

Additional Commercial Products:

The Compucyte's laser scanning cytometer technology grew out of the original high-content cell analysis technology: Flow Cytometry by using fluorescence and laser light scattering methods, and then analyzing that data with powerful graphical software tools to obtain meaningful population-based information. The system will not perform chromogen based brightfield cell analysis. The newer system called iColor will perform cell analysis using combined fluorescence and chromogen stain but is still a cell based system using segregated cells in a proprietary cell well substrate. It does not perform on a regular tissue immunohistochemistry stained slide which is the current state of art in pathology practice.

The Chromavision ACIS, with some of their patents described above, could do many slide based analysis but has limited the population statistic analysis to getting pixels that are positively stained in hot spots areas and over all the area of the image frame. It uses an RGB color ratio and color transform as well as lookup table and work with single pixels, not single cell analysis. The percent obtained in their instrument relate to percent area of the image.

Since the invention may be seen as similar to Chromavision, ACIS, we extract the relevant article that separates our invention. We do not use RIB ratio but uses a different method of extracting separately the blue and red thresholded objects, work on this local regions of interest and not on the total frame, and perform a dynamic color and intensity segmentation on these thresholded bitplane binary objects. Furthermore, it is clear that their technique is an estimation based on the area and the average size of cell nuclei, which clearly departs from our single cell technique. Their R/B ratio technique is stated herein for reference:

"Thus, the pixels of a cell of interest which has been stained contain a red component which is larger than either the green or blue components. A ratio of red divided by blue (R/B) provides a value which is greater than one for tumor cells but is approximately one for any clear or white areas on the slide. Since the remaining cells, i.e., normal cells, typically are stained blue, the R/B ratio for pixels of these latter cells yields values of less than one. The R/B ratio is preferred for clearly separating the color information typical in these applications. Since it is of interest to separate the red stained tumor cells from blue stained normal ones, the ratio of color values is then scaled by a user specified factor. As an example, for a factor of 128 and the ratio of (red pixel value)/(blue pixel value), clear areas on the slide would have a ratio of 1 scaled by 128 for a final X value of 128. Pixels which lie in red stained tumor cells would have X value greater than 128, while blue stained nuclei of normal cells would have value less than 128. In this way, the desired objects of interest can be numerically discriminated. It has been found that normal cells whose nuclei have been stained with hematoxylin are often quite numerous, numbering in the thousands per 10. times. image. Since these cells are so numerous, and since they tend to clump, counting each individual nucleated cell would add an excessive processing burden, at the expense of speed, and would not necessarily provide an accurate count due to clumping. The apparatus performs an estimation process in which the total area of each field that is stained hematoxylin blue is measured and this area is divided by the average size of a nucleated cell. By dividing this value by the average area for a nucleated cell at 350, and looping over all fields at 352, an approximate cell count is obtained. Preliminary testing of this process indicates an accuracy with +/−15%."

The ARIOL system of Applied Imaging uses automated slide delivery to microscope and performs similar capacities as the Chromavision. It has been using the pixel mask technology and because of similar accuracy issues has not implemented its population statistic reporting.

PAXIT has a limited module to do population statistics but only appears to count the positively stained cells in a nuclear pattern, not in a single cell mode.

Imaging flow cytometry U.S. Pat. No. 6,251,615 will not allow visualization of routinely immunohistochemically stained cells in brightfield microscopy but uses fluorochrome reactive antigens and fluorescent microscopy displayed cells. An example is ImageStream® 100 Imaging Flow Cytometer which is high-throughput system (200 cells/second) that generates brightfield, darkfield and up to four fluorescent images, but will not perform single cell analysis on routinely immunohistochemically stained slides.

It has been found, however, that present prior art apparatus and methods fail to meet the demand for a low cost, efficient, customizable imaging microscope that is capable of extracting or overlapping, concurrent data acquisition and analysis over color image obtained by brightfield light. A problem found in alternative systems is that they are capable of imaging a set of pixels representing the stained object over all the other digital objects in the image frame which is not an accurate representation since some microscopic images contain background stromal tissue or other cells other than the relevant class. Examples of these other objects include stroma, blood vessels, large cancer cells if the target cells are the tumor reactive lymphocytes, fat and serum protein spaces. Another problem with available systems is the need for special filters, reliance on machine obtained hot spots and non-biased approaches, and complexity in the system optics is required, increasing the complexity to user and system.

OBJECTS AND ADVANTAGES

Accordingly, besides the objects and advantages of the "virtual flow cytometry" on a slide in our above patent, several key objects and advantages of the present invention include:

a) Use of routine immunohistochemistry slide readily available in the diagnostic laboratory for pathologist and scientists.

b) Use of routine diagnostic microscope with outfitted CCD RGB camera available in most pathologists or scientists office.

c) Use of single cell image analysis result instead of the prior art pixel and area-based image analysis. The object advantage of the invention overcomes these difficulties by using single cell population statistic detection to detect the whole cells, membrane cytoplasm nucleus and all, irregardless of color mixtures inside the cells. The frequency distribution of variable staining single cells is displayed for the user. Optimal evaluation of these results are then rapidly visible and accessible for approval or system modification based on the actual visualized original tissue and cell distribution in the colored image.

d) Use of a single cell graphic plot only made possible by the single cell image analysis technic to display the features of the collections of cells in tissue with an objective display of feature distribution data, verifiable and modifiable by the user.

e) Use of a novel thresholding algorithm that dynamically adjust for staining and sectioning variabilities by using the novel epsilon parameter.

f) Use of a novel thresholding algorithm that dynamically adjust for a wide range of light intensity of the transmitted light microscope by using the novel epsilon parameter.

g) Use of the combination of the above to provide a new and improved apparatus and method that converts tissue immunohistochemistry results to a data and display, commonly ascribed to a prior art flow cytometry apparatus.

Slide based Tissue Cytometry as being described herein will aid in slide based diagnosis in providing a "flow cytometry"-like function to histochemically or immunohistochemically stained cells fixed on a microscopic slide.

We approach image analysis in more objective, intuitive, and specific manner than prior art by limiting results to member of the same class of cells. Since this approach is a prerequisite of a "virtual flow cytometer", we therefore automatically segmented stained cells apart from the tissue stroma and apart from other cells and calculated the percentage in a class of immunostained cells over the non-immunostained members of the same class. Class membership is determined using size and morphologic criteria along with the counter stain and immunostaining result.

The single cell approach for determining members of the same class required us to develop a simultaneous double thresholding method to extract the same class of cells. The novel dual segmentation technique using the built in CCD hardware allowed us to perform this function.

Our approach is advantageous than prior art because there is no need to use an expensive imaging spectrometer or spectral microscopes as one may approach the variable color segmentation problem. Moreover, there is also no need to identify pure color and measure color differences as colors are often mixed in tissue; brown is often with blue, and chromogen and dye bleed into each other as a rule. There is also no need to have a special light such as UV or confocal optics. An ordinary microscope with camera using brightfield microscopy is all that is needed for obtaining the images. In the preferred embodiment of the invention, colored component can be better analyzed if color is separated from the intensity component. This is because the relevant objects are often darker than surround. (Cytometry 39:275, 2000,Batchelor and Whelan 1995, PSPIE :2347).

Recognizing the limitation of the RGB image analysis approach where intensity information is not separable, we resorted to using a combination of hue and intensity information on a limited defined subset of image or region of interest, further optimized by visual feedback and solved the problem of accurate population statistics of chromogen-stained tissue on microscopic slides.

REFERENCES TO SPECIFIC DOCUMENTS RELATED TO THE INVENTION

| 6,692,952 | Feb. 17, 2004 | Braff, R. | MIT |
| 6,294,331 | Sep. 25, 2001 | Ried, T. | USA |

-continued

REFERENCES TO SPECIFIC DOCUMENTS RELATED TO THE INVENTION

| 6,215,892 | 2001-2004 | Douglass, J. | Chromavision |
| 6,418,236 | 2002-2007 | Ellis, B. | Chromavision |
| 6,404,916 | Jun. 11, 2002 | De La Torre-Bueno, J. | Chromavision |
| 6,337,472 | Jan. 8, 2002 | Garner, H. | Univ. of Texas |

OTHER REFERENCES

R. M. Haralick et al., IEEE Transactions on Pattern Analysis and Machine Intelligence, PAMI 9:532-550, 1987.

Elie et al. A simple way of quantifying immunostained cell nuclei on whole histologic section. Cytometry, 56A: 37-45, 2003.

Whelan, 2001 Machine Vision Algorithm in JAVA, Springer.

Russ J C, The Image Processing Handbook. 2nd Ed., 1995, Boca Raton, Fla., CRC Press.

Gonzalez R C, Woods R E. Digital Image Processing. 1992. Reading Mass.: Addison-Wesley, 716.

Johannsen G, Bille J. A threshold selection Method Using Information Measures. Proc. of the $6^{th}$ Int. Conf. on Pattern Recognition Munich, Oct. 19-22, 1092, p. 140-142.

Ridler T W, Calvard S. Picture thresholding using iterative selection method. IEEE Trans. On Systems, Man, and Cybernetics, 1978. SMC-8(8):p 630-632.

Otsu, Nobuyuki, "A Threshold Selection Method from Gray-Level Histograms", IEEE Transactions on Systems, Man. and Cybernetics, vol. SMC-9, No. 1, January 1979.

Standardization and Quantitation of Diagnostic Staining in Cytology," edited by M. E. Boon and L. P. Kok.

Bacus, James W. and Les J. Grace, "Optical Microscope System For Standardized Cell Measurements and Analyses", Applied Optics, 26:16, pp. 3280-3293, Aug. 15, 1987.

Armitage J et al., Int Lymphoma Study Group, Blood, 1997.

Digital Image Processing. G. A. Saxes, John Wiley & Sons, 1994, pp. 127-137.

Vincent L, Soille P. Watersheds in Digital Spaces: An Efficient Algorithm based on Immersion simulations. IEEE Trans on Pattern Analysis and Machine Intelligence 1991; 13:583-598

Definitions of Terms

A digital image will be defined for the purposes of describing the invention as a two-dimensional collection of points with intensity I (x,y) at coordinates (x,y). Color images are replaced with color RGB(x, y) at coordinates (x, y).

A histogram of a picture is a plot of intensity or color versus the frequency of occurrence. The range of intensity of a picture is often small compared to the range available on a system. The global real color image is the ground truth that is referenced by the user to collect histogram characteristics—which generally fall into bimodal or multimodal categories. The multimodal categories of global image lends itself a type of histogram thresholding mode usually by entropy parameter while the isodata parameter worked better with bimodal histograms.

Mathematical morphology is an approach to image processing which is based on the shape of the objects processed. Haralick et al. described in "Image Analysis Using Mathematical Morphology", but the equations have been reformulated based on Boolean arithmetic instead of set arithmetic to facilitate the conversion to computer programs. The following logical operations are used: OR, AND, EXOR for binary images. Dilation is an operation that spreads out the marked pixels and has the effect of reducing noise and filling small holes. Erosion is an operation that contracts the marked pixels and has the effect of thinning the object and expanding holes. The most common dilation and erosion operations have as input an image and a structuring element known as the dilation or erosion mask. The shape of the structuring element known as the dilation or erosion mask depends on the application. Dilation and erosion are often performed in pairs.

Objects Operations and Counting (OOC) usually refers to the techniques of locating marked objects and obtaining information about them. Assume that the pixels in the objects all have value 1 and the background pixels all have value 0. The technique for locating the objects is well known and uses region of interest and the corresponding identified objects represented by bitplanes, masks, or binary objects. The previously processed binary image is scanned until an object pixel (which is the starting pixel for boundary tracing) is encountered.

Hue singularity where the hue and saturation is undefined when RGB=1 or 0, i.e., the darkest and brightest spots, respectively. Many systems fail without removing singularities.

Gray-value morphological processing using iterative Isodata technique was developed by Ridler and Calvard and has appealing functionality in their relative insensitivity to brightness or darkness range of the histogram, but is readily influenced by the histogram shape.

Isodata mode is an automated method. The histogram is initially segmented into two regions using a starting threshold value such as the half the maximum dynamic range. The sample mean associated with the background and foreground pixels are computed for the gray value. A new threshold value is computed as the average of these two sample means. The process is then repeated, until the threshold value does not change anymore. After the algorithm is applied, the population of interest is separated. In our example, we applied this principle to color images, and when the histogram is based on the degree of brown staining or lack thereof, the positive and negative cells are separated as two binary objects.

Gray-value morphologic processing using the entropy thresholding technique was developed by Johannsen G, Bille J. Entropy algorithm is an automated mode that dynamically adjust to the image histogram distribution but is likewise relatively insensitive to the brightness range. The method divides the histogram into two part, minimizing the interdependence between two parts, measured in terms of entropy. The grey level that performs this division will be the threshold value. As a condition, the user may specify the fraction of the image that minimally should be assigned to be a foreground object. The algorithm then searches for the minimal entropy within this constraint. In our example, we applied this principle to color images, and when the histogram is based on the degree of brown staining or lack thereof, the positive and negative cells are separated as two binary objects, with the added bonus of an adaptive parameter in the form of the fraction epsilon.

Bitplane sculpting: In both these isodata and entropy modes, the user specifies the part of the image to consider for the computation of the histogram. In our example, the parts of the image pre-processed by RGB is used, then the intersection of these images are used, then the resulting region of interest are transformed to different color value, and the thresholding is applied to these narrower tier of images. The result of the thresholding operation is stored in one of a number of bitplane images used in bitplane sculpting operations and the value is also stored and accessible.

SUMMARY OF THE INVENTION

The major problem overcomed by this invention was the counting of the positive single cells stained with a marker but also the cells not stained with the monoclonal antibody or probe but only with the nuclear counter stain. In other words, the invention could count the total relevant population and get the numerator and denominator statistics for percentage calculation in that same cell class.

The invention accomplishes the above single cell analysis of the same class of cells by overcoming the challenges in the problem domain. The challenges include 1) simplifying the complex variably lighted and stained images of immunohistochemistry, 2) coming up with a dual segmentation algorithm to solve the dual stained cell problem and using thresholding by similarity type of segmentation, 3) by using color and gray scale segmentation techniques in a new and improved manner. The solutions to these are described in the invention.

The formulation of the "complex images in immunohistochemistry" include the overcoming the staining variability and wide range of lighting with no change in results; and identifying the different colored chromogens and nuclear counter stain dyes; overcoming clumping and detecting the single cells apart from the tissue; detecting single cells that belong only to one particular class to get a class percentage; and integrating these results in daily diagnostic pathology practice so the user could easily use the tool and visualize the results in minimal effort and time. The current invention provided solutions to the above objectives.

BRIEF DESCRIPTION OF THE DRAWINGS

The patent or application file contains at least one drawings executed in color. Copies of this patent or patent application publication with color drawing(s) will be provided by the Office upon request and payment of the necessary fee.

FIG. 8a, 8b, 8c, 8d show the exemplary flow chart of the main algorithm described in detail as follows and in the claims.

DETAILED DESCRIPTION OF THE INVENTION

Figure 1:
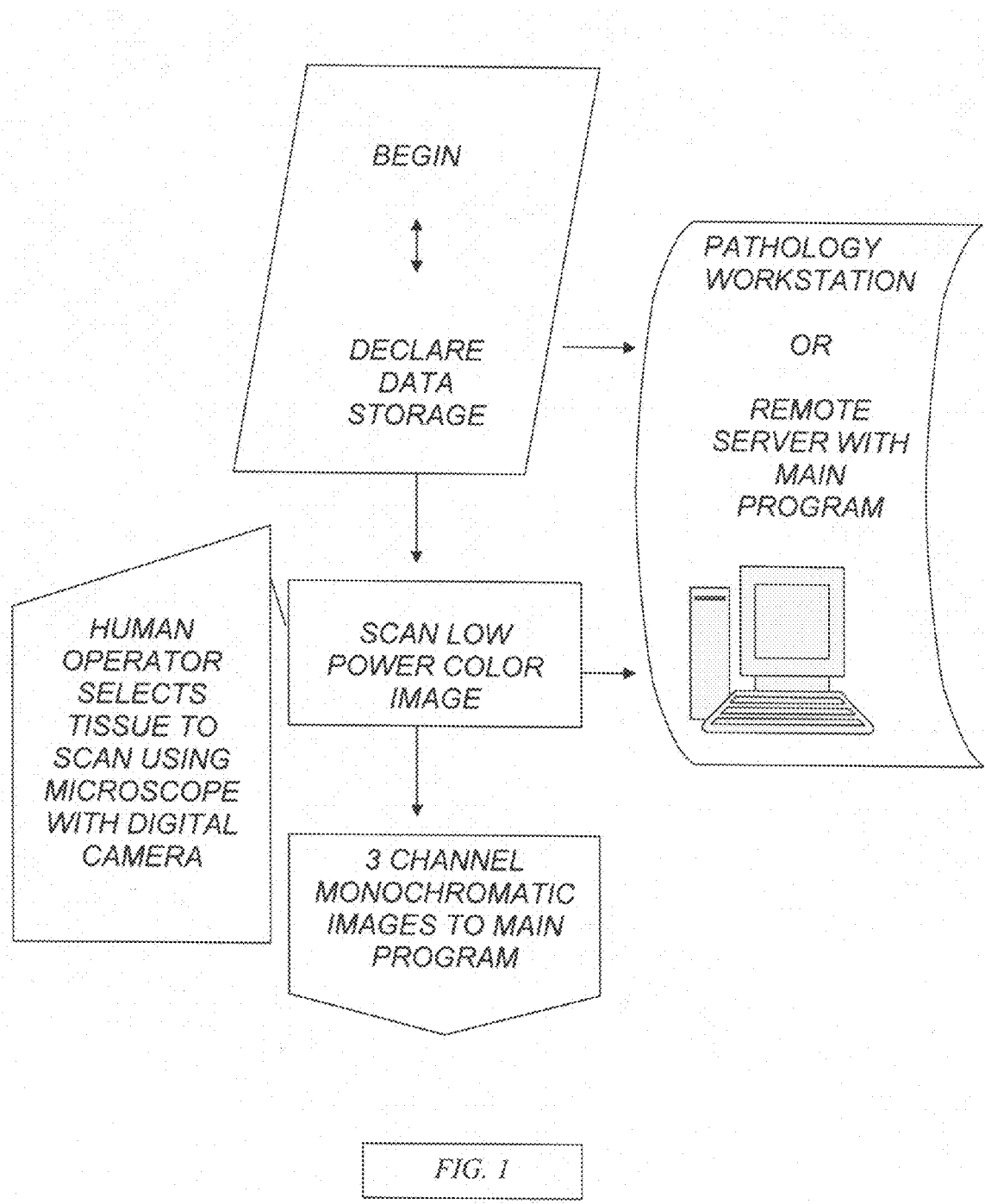
FIG. 1 shows the exemplary components needed to accomplish the processes of the invention.

FIG. 1 is a block diagram of the interface of the system. The system includes a human operator or an automated slide delivery system, to place and select the tissue to scan for low power color image. The image is scanned of 3 channel RGB monochromatic planes which are sent to the main program. The main program and its data storage are in preferably a pathology workstation with monitor display or alternatively located in a remote server.

Figure 2:
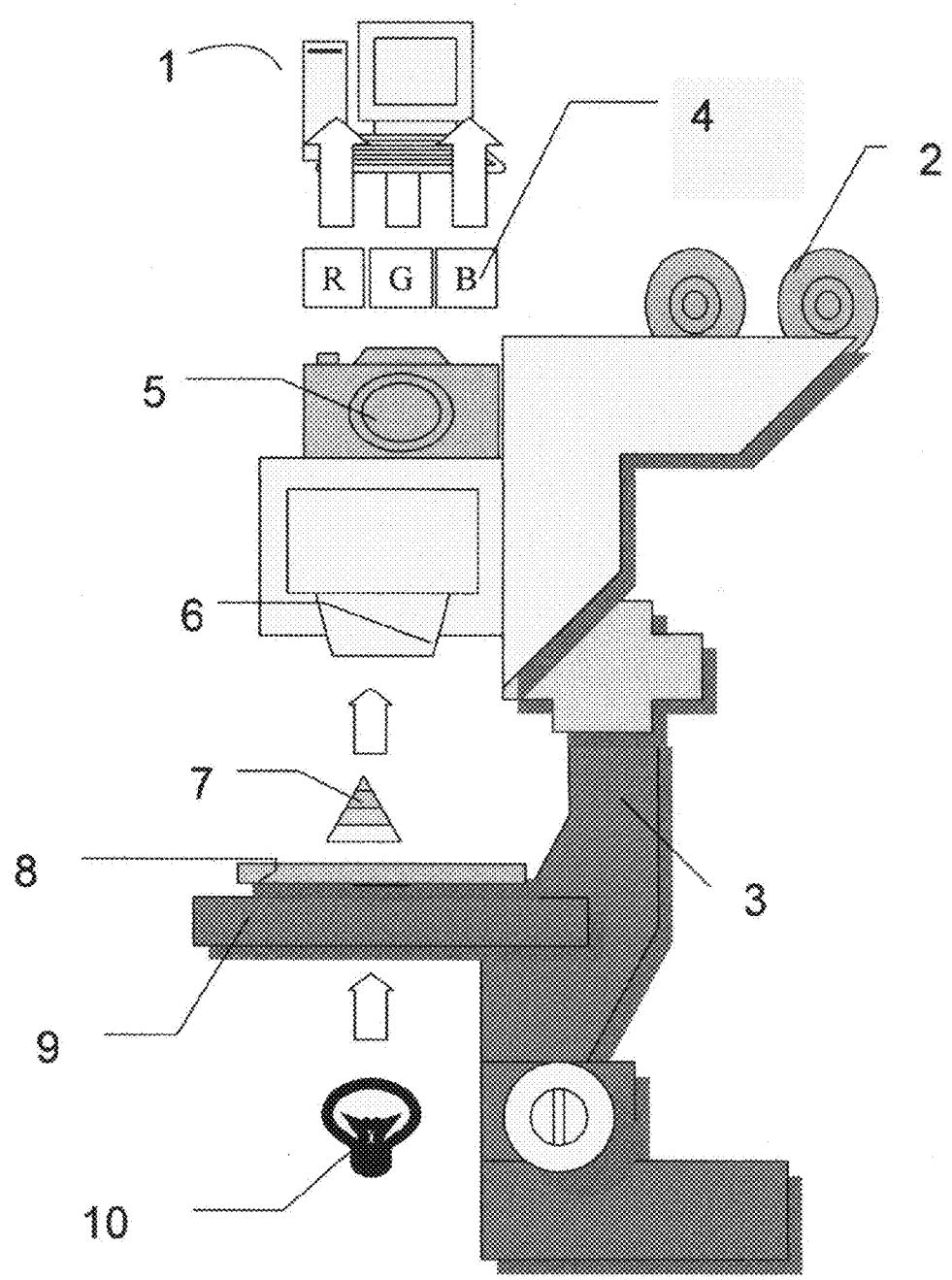
FIG. 2 shows the exemplary microscope and CCD camera and digital image obtained from tissue on microscopic slide.

The general purpose computer 1, preferably a personal computer (PC) FIG. 2 controls the operation of the image processor board preferably a Pentium with PCI bus advanced chip, running Windows 9× or greater or a PowerPC with PCI bus running OS 8.5 or greater and able to run executable programs. The frame memory of the image processor is memory mapped to the PC which performs most of the complicated computations that the image processor cannot handle. This includes searching and other operations requiring random access of the frame memory. With careful planning, the image processor can perform selected functions in parallel with the computer. The use of a PC also facilitates the transfer of data to other software packages that are readily available. The user interacts with the computer via a keyboard and a mouse. An industry standard interface circuit and ports with software to connect to the internet is preferred. The output device is provided to allow the user to view the data and the results obtained. A graphics color monitor and printer capable of displaying the entire video frame is required.

FIG. 2 show a microscope 3, a color CCD camera 5, a general purpose computer 1 equipped with a special purpose image processing board, and an output device 1 such as graphics monitor or printer. Each of the different components will be discussed in greater detail below.

The trinocular microscope 3 is equipped with set of eyepiece objectives 2 for the human operator to visualize the image obtained from microscopic slide 8 on stage 9 and illuminated by a stable light source 10. The operator focuses the slide view wherein the white spectrum of visible transmitted light image 7 is on focal plane of the eyepieces field of view located above 2 and on the imaging plane of the camera 5. The microscope is equipped with a plurality of objective lenses 6 to perform a plurality of magnifications; with 20.times objective the preferred embodiment because of optimal level of cell detail obtainable with this objective magnification. The image from the CCD camera 5 is funneled in 3 channels representing the blue, green, and red monochromatic image planes, respectively.

The camera 5 is directly connected to a regular trinocular microscope 3 via an optical tube such as a trinocular head, and in alignment with the optical path of the transmitted image of the tissue on slide 8 thru the two objectives 2 which are also integral part of the trinocular head. The camera 5 is preferably a 3 channel CCD RGB camera with separate outputs into 3 channels corresponding to red, green, and blue monochrome images. Preferably, the sample image could be saved as 24 bit depth in RGB color. A CCD chip with a 3 channel 1600×1200 active pixels (1.2 million) CCD (Charge-Coupled Device) with 7.4 um square pixels KAI as sold by Diagnostic Instruments. The bit depth is sampled at 30 bit RGB and could be saved as 24 bit or more for enhanced sampling of details. The overall operation of CCD equipped cameras is well known in the art. The camera image could be saved as 512.times.474 pixels or any other predermined spatial format to be used in the analysis.

The output of the camera 5 is digitized and stored for reference and manipulations. This task is accomplished by an image processor board contained within the general purpose computer 1. Alternatively, the image processor capable of supporting 24 bit RGB of the desired monitor, can take the form of a separate unit coupled to the general purpose computer 1. An image processor preferably is a single board, real-time image processor designed to be interfaced with IBM PC-AT's and compatibles, via a preferred PCI bus card, although other image processing devices may be readily employed. The image processor could at least digitize 512.times.474 pixel images from the camera with 8-bit precision (256 gray levels) per channel. The video card software driver should be capable of saving images in a plurality of standard image file formats, including TIFF, JPEG, PICT and others.

Figure 3:
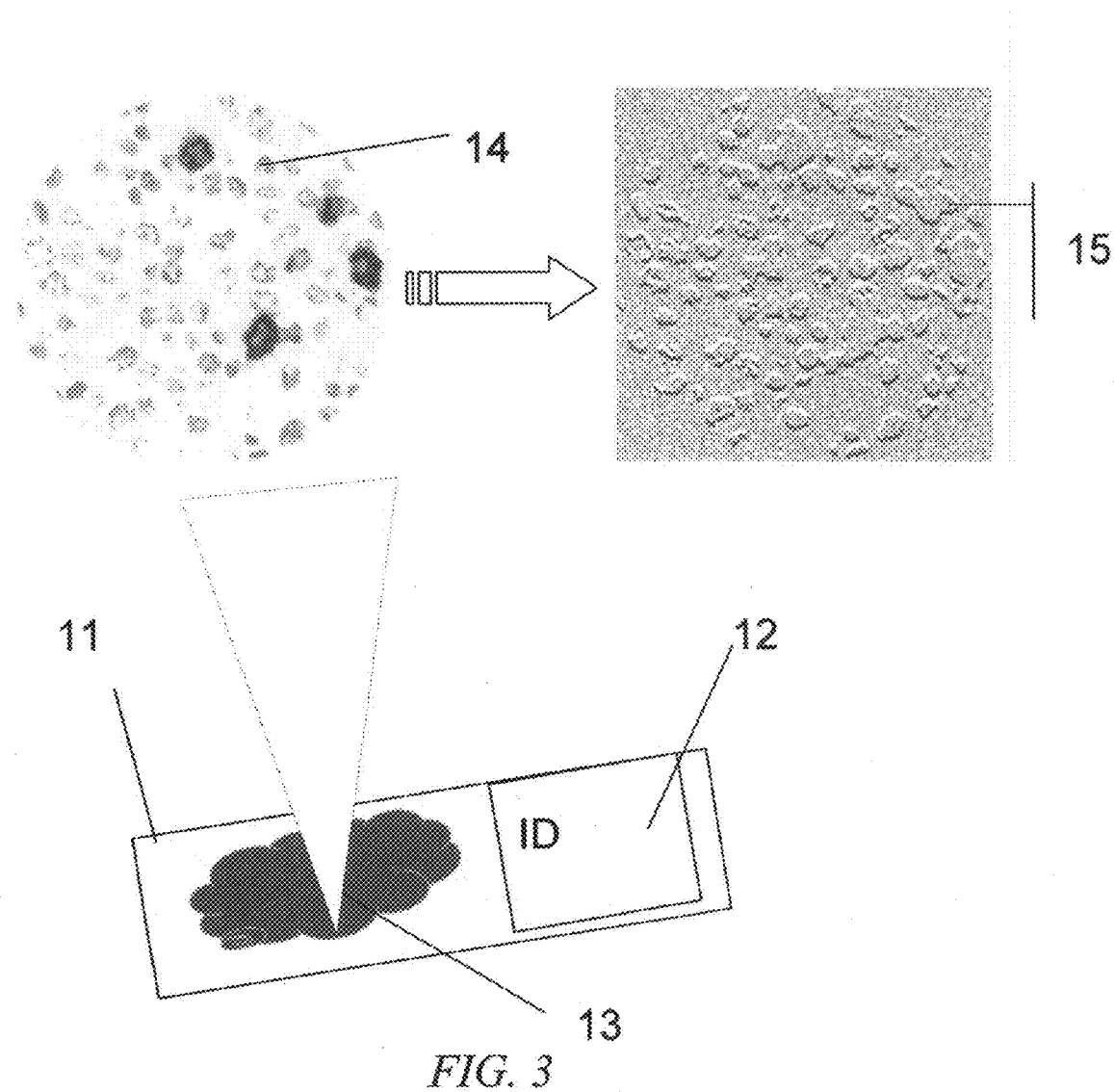
FIG. 3 shows the exemplary tissue on microscopic slide and the magnified microscopic image of cells depicted as tangential three dimensional cut sections of variable sizes corresponding to a single cell object events.

The tissue and slide component is shown at FIG. 3. Current algorithms aim to extract a precise cell boundary for mensuration especially relevant in cytologic images. Given that the cell boundary in tissue section is already artifactually chopped into cell tangents and is partly representative of the whole cell, the issue of accurate edges is answered in practical way. In FIG. 3, slide 11 contain on its surface a cut section of tissue 13 identified as belonging to a patient identified by ID 12. The projected microscopic color image 14, visible in previously mentioned microscope objectives and monitor, displays the blue and the brown cell objects of interest. These objects in reality are 3 dimensional cut sections of whole cells illustrated by the bas-relief 15 showing variable sized cell sections. These objects represent the counts or events to be analyzed but do not represent the exact boundaries or contours of the whole cells. In reality, given enough circular samples from a spherical form of a cell, the modal maximal diameter value should represent the actual diameter. We differ from previous art, such as those that are imaging cytology and therefore whole cell on slides, by considering these diameters as events but more similar to flow cytometry cell events.

Figure 4:
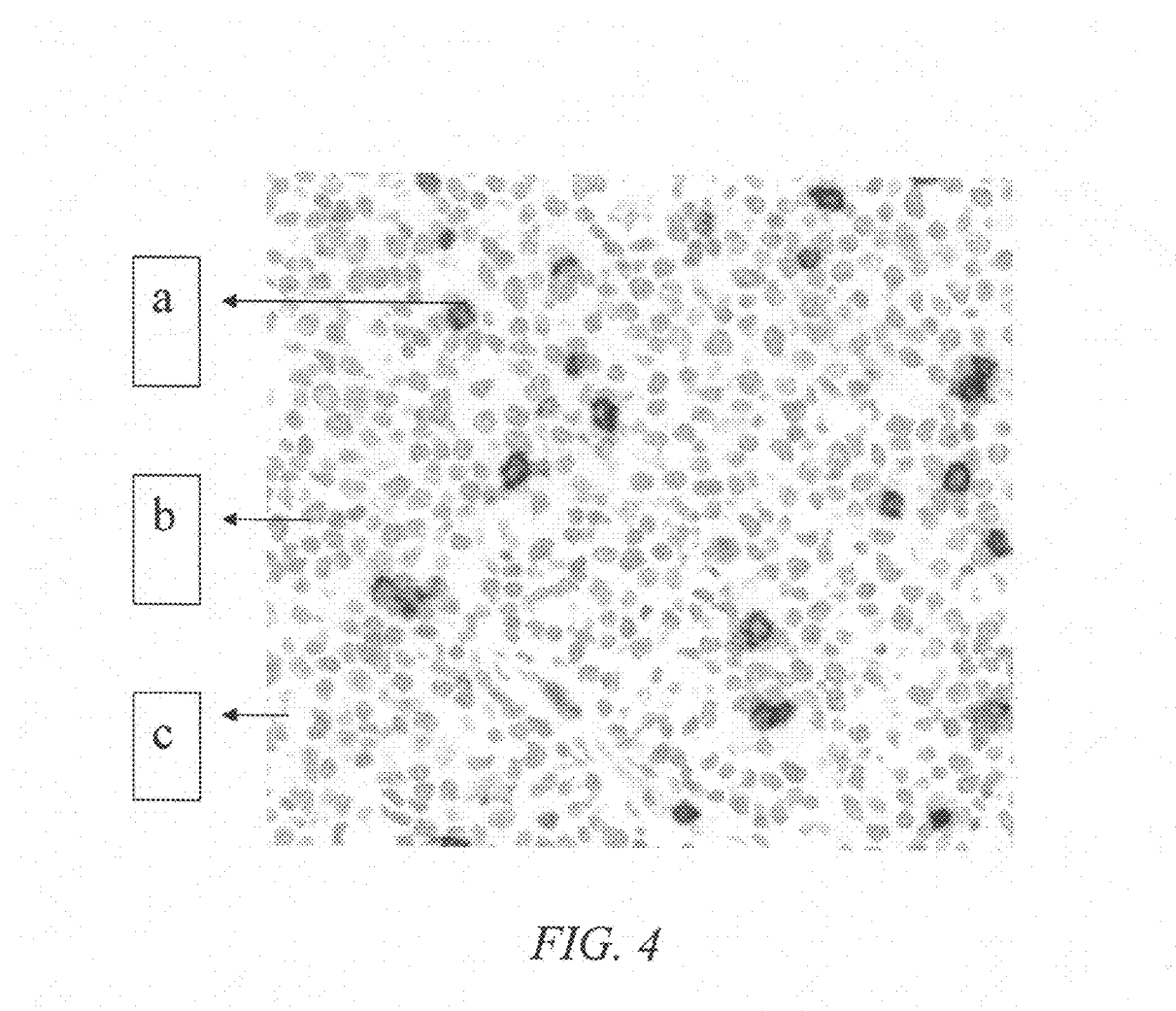
FIG. 4 shows the exemplary true color image frame 512× 474 pixel resolution of the microscopic section containing objects of interest including the brown decorated objects(a), the blue color objects (b) and the interobjects surrounding fuzzy colored or clear spaces (c).

In FIG. 4, is a tissue frame showing the cell objects elements: immunoreactive cells colored brown 4a, the non-immunoreactive cells of the same class stained in hematoxylin shown in blue 4b and the irrelevant non-cells objects and spaces 4c are shown. In the preferred embodiment, the cells are marked with brown chromogen indicium marker and the nuclei are marked with blue hematoxylin dye. It is to be understood that these indicia markers are not limited to these colors but to other dyes as well. In this preferred mode, the monoclonal antibody tagged with brown chromogen (i.e, Diaminobenzidine) or alternatively red chromogen (alpha aminoethyl carbazoyl, AEC) are for a cell specific identification and the tissue cells reacted to a non-specific nuclear counterstain dye (i.e., hematoxylin) visualized as bluish. Other counter stains may be used and the algorithm is extensible to correspond to alternative color mordants.

A preferred embodiment of the cell indicia marker and dye is further described as follows. The marker and dye staining techniques may be broadly classified in at least three categories:

1) Immunohistochemical staining, which may be based on monoclonal antibody attraction or reaction; Examples may be brown or red chromogen or enzymatic alkaline phosphatase or diaminobenzidene alkaline peroxidase.
2) DNA chemical conjugation, such as Feulgen staining, and characterized by covalent binding, with acid hydrolysis of DNA; Examples include Thionin for the Feulgen staining technique for nuclear DNA and DAPI for nuclear reaction.

3) Nuclear counterstain using cytochemical electrostatic interaction indicated by dye-nuclear chromatin reaction. Examples: Fast Red, ethyl green stain, hematoxylin, methyl blue or eosin. The sources of staining affinity noted above are referred to as stain-cell attractive forces. A more expansive discussion of staining and staining mechanisms may be found in "Standardization and Quantitation of Diagnostic Staining in Cytology," edited by M. E. Boon and L. P. Kok.

The calibration material in slide 11 is provided for review by the operator or analyst and include a standard positive control and a chromogen-antigen complex. These items are used to establish a calibration or reference position prior to analysis of the unknown cell or specimen 12. This positive control tissue is places adjacent to 13 or a peptide chromogen complex dot plot standard is also adjacent to 13. As shown in FIG. 3, slide 11 has specimen cell objects 13 positioned thereon for simultaneous staining of collections of cells. This simultaneous staining of both the calibration material and the cells under analysis 14, permits comparison of these two classes or groups of cells to a predetermined and stored reference light intensity, gray level or optical density, of the control cell objects and calibrator dots after staining. If the cell objects are stained either too lightly or too heavily, the difference can be compensated for during the quantitative analysis.

In FIG. 4, the representation of a particular antigen site specified by the user is cell 4a which is brown labeled as marked and amplified. One preferred reaction is as follows: the site is antigenic against a primary antibody bound to a bridging antibody against the primary antibody is used to bind to the primary antibody, and has affixed a Biotin molecule. Avidin-Biotin complex, including an Avidin and Biotin molecules, the latter are conjugated with molecules of either a DAB or alkaline phosphatase AP enzyme. The fourth Biotin molecule site is open for binding the complex to the bridging antibody. When a dye, such as fast red molecules in solution, is added to this mixture, the alkaline phosphatase reacts with the dye molecules to produce insoluble fast red molecules, which mark the antigen site. While this Avidin-Biotin complex is exemplary, any number of marking techniques and stains may be utilized, as noted below. Alternatively, a bridging or sandwich antibody, which is peroxidase-anti-peroxidase, will be utilized and amplified by DAB in the previously-described manner.

In the above-noted methods, the apparatus for the present method provides a dual thresholding method to distinguish the areas stained by the brown chromogen [cytoplasm] and the areas stained by the blue hematoxylin [nucleus]. These different images, one provided by the blue channel and the other by the red channel, separate the brown stained cells from the blue stained cells, the former which contains the specific antigen, and also separates both areas from other cell or field features, and the latter cells without the specific antibody reaction. The method uses contrast thresholding by CCD using the differential histogram distribution of the cell objects located in the blue channel and those located in the red channel thresholded initially by isodata mode.

Image Processing Method

The invention uses multiple layers of processing. As image data passes through various stages, with each stage applying bitplane sculpting for thresholding providing finer and finer discrimination of objects from non objects. The method uses a novel multi-stage thresholding and segmentation algorithm based on multiple color channels in RGB and HS I spaces. The algorithm uses auto-thresholding on red and blue channels in RGB to get the raw working image of all cells, and then refines the working image with thresholding on hue and intensity channels in HS I, and further separates different classes of cells by auto-thresholding within the working image region.

FIG. 1 shows the initial steps of the invention with human input and human reference for the "ground truth" that does so in FIG. 2 by either looking under the objective lenses 2 or by referring to image in the display monitor in 1 after focusing the microscope and adjusting for the optimum light setting, this subject treated more below. In one embodiment of the invention, the computer system 1 processes a 20.times. Magnification field of view (FOV) to be displayed after processing in CCD camera 5.

As some control is necessary to avoid camera saturation, or inadequate exposure in any one of the color bands, balancing is performed automatically by utilizing a white light calibration by obtaining first an image of clear slide 11 in location without blemish or without tissue 13 and using the software for setting the white balance before human operator starts using this system. In addition to setting the light balance, a preferred embodiment is for setting a positive chromogen calibrator for stain density to be scanned. The calibrator is located alongside the tissue on slide 11 to be used to plot a standard linearity graph performed by the alternative module in software. The graph is based on a predetermined antigen density corresponding to 1+ to 4+ ranges. These calibrator images per slide are stored as a lookup table. Alternatively, by automated scanning means, the calibration is performed beforehand using an automated slide delivery and imaging system. The system description is beyond the scope of this invention but is preferably one like the Vision Biosystem SL50.

The image scanning begins by providing for a plurality of scanned images from the microscope 3. A preferred embodiment includes a software module with calibrated brightness filter to get the optimum light exposure. The human operator or the automated delivery system has to also set the optimal transmitted lighting using a rheostat mechanism controllable to a predetermined range of brightness. In one embodiment, the brightness is set using an Olympus microscope equipped with a 30 watt halogen light source and a range of setting from 1 to 10, to a range between 5.5 to 6.5 on the dial. This setting is optimal even though image analysis on test systems was stable with a rheostat setting from 4.0 to 7.0. We also found that image analysis results are stable even without a blue 80A Tiffen filter, when the condenser is down, or when the light bulb is just replaced with a new one. In those extreme settings, the whole image goes from yellowish saturation to bluish saturation from low to high number of rheostat respectively. Because of the robust automation that adjusts to the feature inherent in the image, the results are noted to be accurate despite the brightness variation in contrast to prior art results which are exquisitely sensitive to brightness variance. Preferably, our algorithm has, outside this predetermined range of light intensity, a trigger for an error signal or prompt for correct adjustment.

A typical imaging system may use an incandescent halogen light bulb as a light source. As the bulb ages, the relative amounts of red and blue output can change. The tendency as the bulb ages is for the blue to drop off more than the red and the green. To accommodate for this light source variation over time, white balancing process as described above. The brightness of an image is provided by histogram fluction determines how many pixels within a gray scale FOV have a certain image intensity and cut off values of too dark or too bright are predetermined to warn the user of suboptimal lighting of the images. This procedure is preferably using a wide range of 120 and 230 as brightness cutoff over a range of 256, of low and high end respectively. The optical density of the total pixel of the grabbed image are summed up and averaged to give the mean brightness. The total pixel number is divided by the mean brightness to give the total average frame brightness. This value is used as the cutoff.

In FIG. 4, as one exemplary drawing, the whole color frame of the source image shows the chromogen-brown marked cells (a), the unmarked blue stained nuclei of relevant cells (b), and the intervening sea of whitish or dirty yellow spaces representing the unstained intercellular spaces (c) that are used in analysis to define objects and to define non-objects to be removed from the scene as irrelevant pixels. The first processing step result is shown in FIG. 4 which is the result of image capture and display to visualize and process the 20.times image frame. This image is used in pre-segmentation step that identifies candidate objects of interest, or potential cell nuclei. The 20.times. magnification images are obtained at pixel size of about 0.55.times.0.55 microns. In this preferred set-up, the calculation of the conversion from area to microns diameter is as follows. For the image frame using the above 20× set up, the pixel size converts to ⅔ microns per pixel in the previously described preferred CCD chip. Other CCD chips are easily configured based on the specification by use of a micrometer slide calibrator known in the microscopy art. The conversion factor P will be changed accordingly. The formula below was used to convert pixel area to cell diameter in microns This information is stored for later retrieval as per single cell data in the abscissa axis (Y data):

Cell diameter=2*(sqrt of (Area in pixels/π))/1.5=sqrt of (Area in pixels*$P$);

where diameter is in microns, P is conversion factor (0.56588424212)

The intensity component of the colored blue and brown objects were summed up per cell object, averaged, and stored as average stain density. This information is stored for later retrieval as per single cell data in the ordinate axis (X data).

The computer stores the address of the memory location where the results structure resides. This memory will be filled with the results of the invention directly using the algorithm in FIG. 8 and in summary arriving at the final objective. The FINAL RESULTS of the computer system 1 running the algorithm in FIG. 8 are outputs based on the above set of X and Y data and concludes with the counts of stained cell number over all the total cell numbers and result in a table or graphic plot of size vs. optical intensity or stain density.

For a better understanding of the following descriptions, we preempt the technical description at this junction and show the individual objectives of the single cell image analysis algorithm as follows:

SEGMENTATION SINGLE CELL OBJECT STAIN INTENSITY
SEGMENTED SINGLE CELL OBJECT COUNT AND SIZE IN MICRONS
THE NUMBER OF OBJECTS THAT WERE SEGMENTED IN THE FOV.
ESTIMATED CELL COUNT OF STAINED AND NON-IMMUNOSTAINED CELLS

This number may be slightly different from the number manually counted since objects that are too close, too big, too small, or on to the edge of the frame are not classified.

Figure 5:
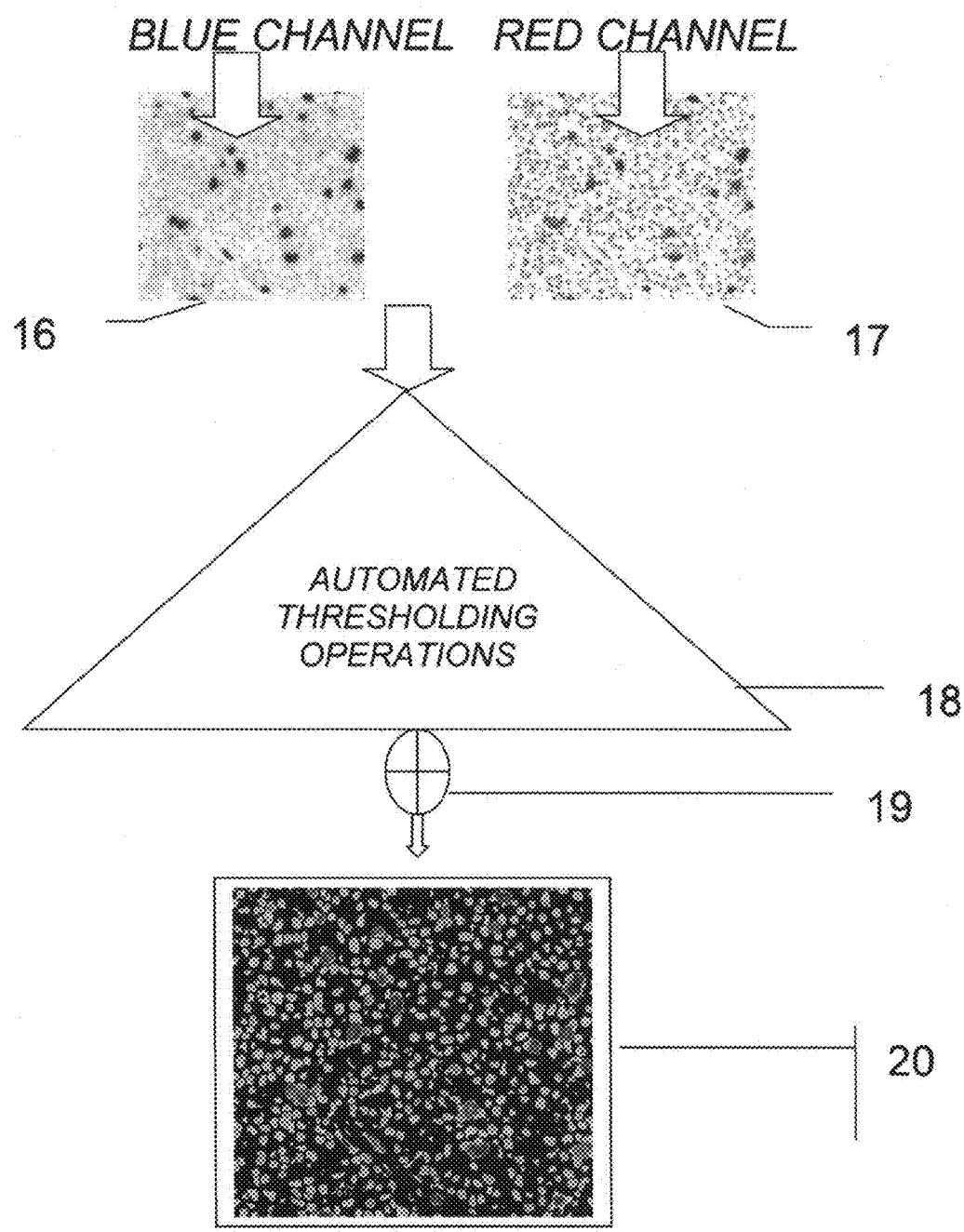
FIG. 5 shows the exemplary method in thresholding the gray scale products of the blue and red channels and combining the results to yield the total working image containing the raw brown and blue stained cell objects.

Returning to the second step, shown in FIG. 5, is the blue 16 and red 17 monochromatic images which are the data used in the double thresholding technique. In the preferred embodiment, enhancing the color information is performed by processing first a single color channel from the camera using a predetermined channel image. As an example, consider a blue channel 16, in which objects that are brown are relatively dark and objects which are blue, or white, are relatively light. In contrast, the red channel enhances both the blue and the brown objects.

Detailing more on the CCD enhancement in FIG. 5, the one alternative embodiment is a separate apparatus of the invention that first enhances the contrast between potential objects of interest and their backgrounds: bright areas become brighter and dark areas become darker. This phase of processing creates an enhanced image 16,17. During image thresholding 18, a threshold test identifies objects of interest and creates threshold intermediate images in method in processes 18,19. The threshold intermediate images, now assigned to labeled bitplane masks, are applied to the original color image FIG. 4 to generate reference true color objects for user validation. The automated histogram thresholding also performs equalization using percentile thresholding known in the art, as an alternative embodiment to including software or hardware low pass filter, contrast enhancement or histogram equalization as pre-processing step.

The dual binary images resulting from processing images 16,17 represent the red channel threshold and blue channel threshold objects and are treated as raw threshold bitplane mask representing positive and all cells-are combined using Binary OR. In addition, the percentage of the bitplanes thresholded from blue channel objects over the binary OR products in bitplanes R and B, described in drawing FIG. 8a, as calculated from 16, 17 binary images, provided the epsilon parameter ξ which will be used later on for entropy thresholding the hue and intensity color space. These thresholded images containing the original colored cell objects processed from blue and red channels, are combined as full color image 20, now including the results of the total of the positive and negative cells. The combined bitplanes R and B are overlayed with original color image for user feedback and labeled as the raw working image color of all the target cells, also referred as such in FIG. 8a flow chart.

Next, the processing bitplane images acquired as in FIG. 5 and processed using the software according to the flow chart in FIG. 8a. are described as follows. This step, preferably uses transformed image of a different color space, such as hue and intensity or hue or value, or L, a, b in the LAB color spaces, which are color spaces, well known in the art. The advantage of any of these spaces is the color information is separated from the intensity or stain density information. After removing the brightest and the darkest 1% pixels from the resulting hue and intensity transformed images, these intermediate images are further processed as follows.

Next, the pixels of the filtered above image are dynamically thresholded to determine the presence of one or more regions of connected pixels having the same color. The dynamic thresholding using the entropy mode, unlike many algorithm in prior art, is very important in the invention in as much as the method relies on the distribution of the hue and intensity values and the algorithm adjust for images that are less than optimal, too dark or too light. To separate objects of interest, the thresholding operation is performed designed to set pixels within cells of interest to a value of 1, and all other areas to 0. Thresholding ideally yields an image in which cells of interest are white and the remainder of the image is black. A problem one faces in thresholding is where to set the threshold level. One cannot simply assume that cells of interest are indicated by any pixel value above the nominal threshold of 128. The objects in the field of view undergo a preprocessing test using threshold to determine whether the brightness of the object lies within a predetermined range. In this mode, thresholding is a doublet process again using both the hue and intensity image planes.

The hue and intensity planes are thresholded using an automated histogram thresholding mode entropy. The entropy mode use a dynamic parameter epsilon to allow for only a fraction of the hue and intensity detected objects to be segmented as objects and this parameter also relies on the frequency distribution of hue and intensity. This mode is adaptable to the day to day cell staining variation. This mode uses image to image math. The result of calculation of two image frames using first the bitplane mask from blue channel divided by the total mask from both the blue and the red channel combined using binary OR. This number is a fraction that is proportional to the entropy mode fractional parameter. The image math result of above is delimited by multiplying with 0.45 and the resulting product is equal to the epsilon. We have observed that this fraction encapsulates the proportional staining of the dark brown objects over the blue objects. This adaptation is a further advantage of this technique over prior art.

In other words, the epsilon is directly related to the output of the red and blue channel thresholding operations, the epsilon encapsulates the highlighted objects both in hue and intensity from the blue channel which happens to be the brown stained cells including its brownish-blue nuclei. Since the epsilon is related to the actual image and its inherent property, epsilon encapsulates the invariant factor which is a novel feature of the invention.

Next, the blue cells are thresholded by using the inverse of the brown linked bitplanes. The brown and blue objects are linked together and holes from nuclei are removed using classical hole removing methods well known in the art, which identify contiguous pixels within objects excluding non-objects.

Next, the identified brown objects are analyzed for stain density by summing intensity values of individual single cells. The resulting objects containing both brown and blue are examined by size criteria according to a set cell diameter, preferably 12 microns when working with cell of lymphocyte class. This size parameter is also user modifiable to effect the thresholding of the alternative cells of interest.

A detail of the summing density is as follows. For the stain density, operations are as follows. The blue threshold image representing brown objects is refined by eliminating holes and eliminating the brightest and darkest of the objects of interest. Small brown objects are linked using a small morphological closing and opening sequence to fill in holes. The mask for the brown objects only is combined with the working image in a binary and processed to yield the intersection containing only those pixels that are both present in the combined images. Thereafter, the total brown stained objects are detected FIG. 6, 21 and named Intermediate Chromogen Objects (ICO) and these objects are stored in memory for future use as numerator. The ICO or its copy, are then subjected to optical density quantitation to yield a density table resulting in a semi-quantitative result from 0 to 4+ based on 25% intervals of optical density. A preferred embodiment is the calibration of the 0 to 4+ range by the internal calibrator standard chromogen loci. Results of the total mean optical density per cell and per total frame are stored for future display. One embodiment of the system stores the results of the optical density per object and used later on for data needed by a density versus size display plot.

Next, any remaining clumps of cell objects of either brown or blue are converted to single cells by repeated thresholding, erosion and dilation combination, the cycles determined empirically by visual feedback. This parameter is kept open to be a user modifiable number. Clumped cell algorithm is as follows. The results of those as previously described in FIG. 5, after automated thresholding 18 and binary OR 19 would contain the total cell working image 20. The working image upon further automated thresholding 18 would yield the brown stained only 21 to be used as a numerator and the total working image 22 as the denominator for the percentage calculation. The clumped cell nuclei are extracted from the only blue objects of procedure following a binary EXOR on the threshold binary image 21 and threshold binary image 22. The result will be all objects except the brown objects. The all blue objects will be subjected to size operation to remove all objects below a certain size (dynamically assigned via computer interactive box) preferably below 12 microns. The remaining objects containing the large clumps are subjected to a watershed procedure using procedures well known in the art including distance transform, ultimate eroded points, and binary skeleton operations to yield more separated objects. These clumps are often minority objects after a predetermined cycle of erosion and dilation or opening and closing operations.

Preliminary testing of our process indicates accuracy with +/−1-4% COV coefficient of variation. Our method is superior over the estimation process of the other proprietary image analysis system in current and prior arts that uses total area of pixels which has a published accuracy of +/−15% (Ellis et al). The described proprietary systems perform an estimation process in which the total area of each field that is stained hematoxylin blue is measured and this area is divided by the average size of a nucleated cell.

In addition, in the present invention, the size factor is also selected by the human operator using a dialog function to dynamically obtain the objects whether the objects are 12 microns or larger, the latter seen in tumor cells and the former often observed in lymphocyte nuclei diameters. The erosion and dilation processes that make up a morphological "open" preferably make small objects disappear yet allows large objects to remain. Morphological processing of binary images is described in detail in Digital Image Processing (G. A. Saxes, John Wiley & Sons, 1994, pp. 127-137).

Next, a cleaning up operation is performed on all objects identified in the red channel threshold binary image are regarded as the total working image contains both the brown, blue, and other objects. These objects are combined in a binary EXOR operation to delete the intersection, i.e., the brown only objects, to yield an image containing only blue objects. These operations to follow aim to refine the blue objects containing the naked blue nuclei, the small tangent sections of nuclei, the bluish small objects from other cells not related to the target cells, i.e., stoma, epithelia, etc. A connected component labeling procedure removes small or oddly shaped objects and assigns a unique label to each remaining connected object.

A morphological closing residue operation known in the art is applied to determine separation boundaries. A separation boundary is subtracted from the hole-filled image to create an overlap of object separated binary image. To ensure that no objects have been lost in this process, the overlap object separated image is dilated to generate an object mask. Small objects not included in the object mask are combined in a set union with the object separation image to provide an object recovered image.

Next, separation of connected objects is as follows. Objects that are larger than a predetermined size are identified and excluded from the image by a connected component analysis operation as described above. To do so, objects in the red threshold binary mask containing blue objects are eroded by a predetermined amount and then dilated by a second predetermined amount. The amount of erosion exceeds the amount of dilation so that objects after dilation are smaller than before erosion. This separates connected objects. A robust industry standard mode of watershed algorithm (Vincent L.) is also additionally applied to finally separate objects that are not separated by the above procedure.

Figure 6:
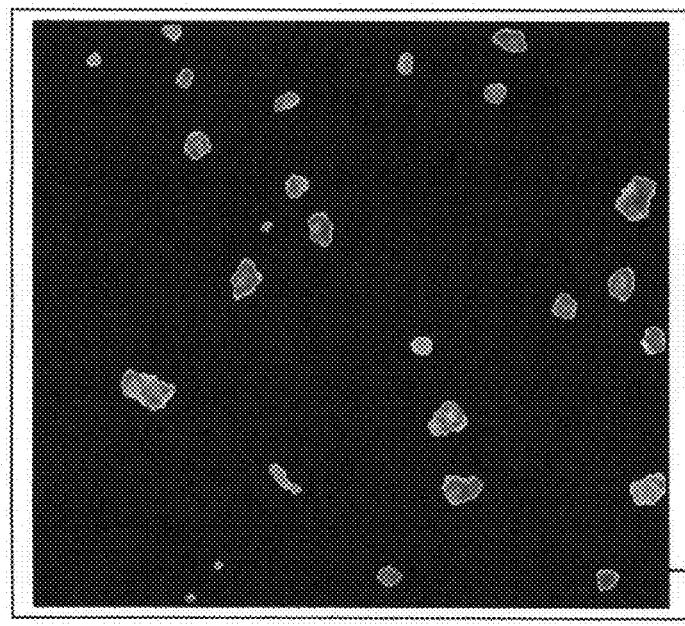
FIG. 6 shows the exemplary brown segmented objects with blue nuclei and the total segmented cells including blue and brown objects representing the numerator and denominator to be used in population statistics in Tissue Cytometry.
Figure 6:
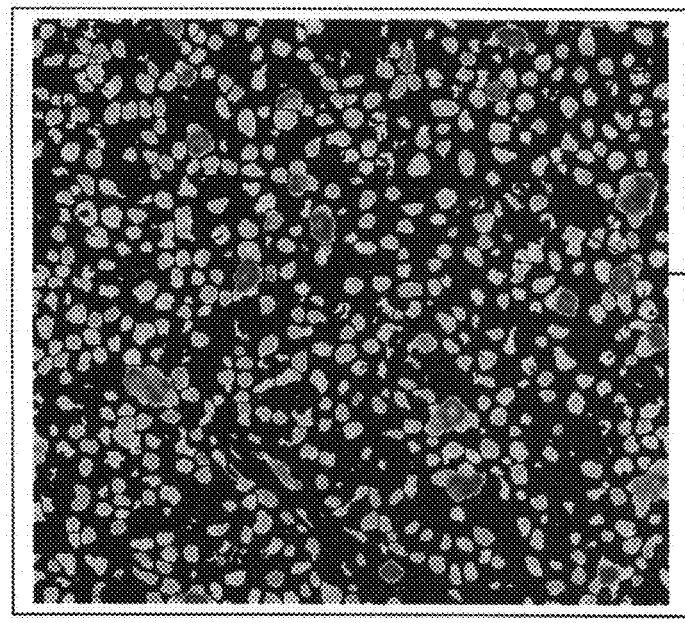
Figure 7:
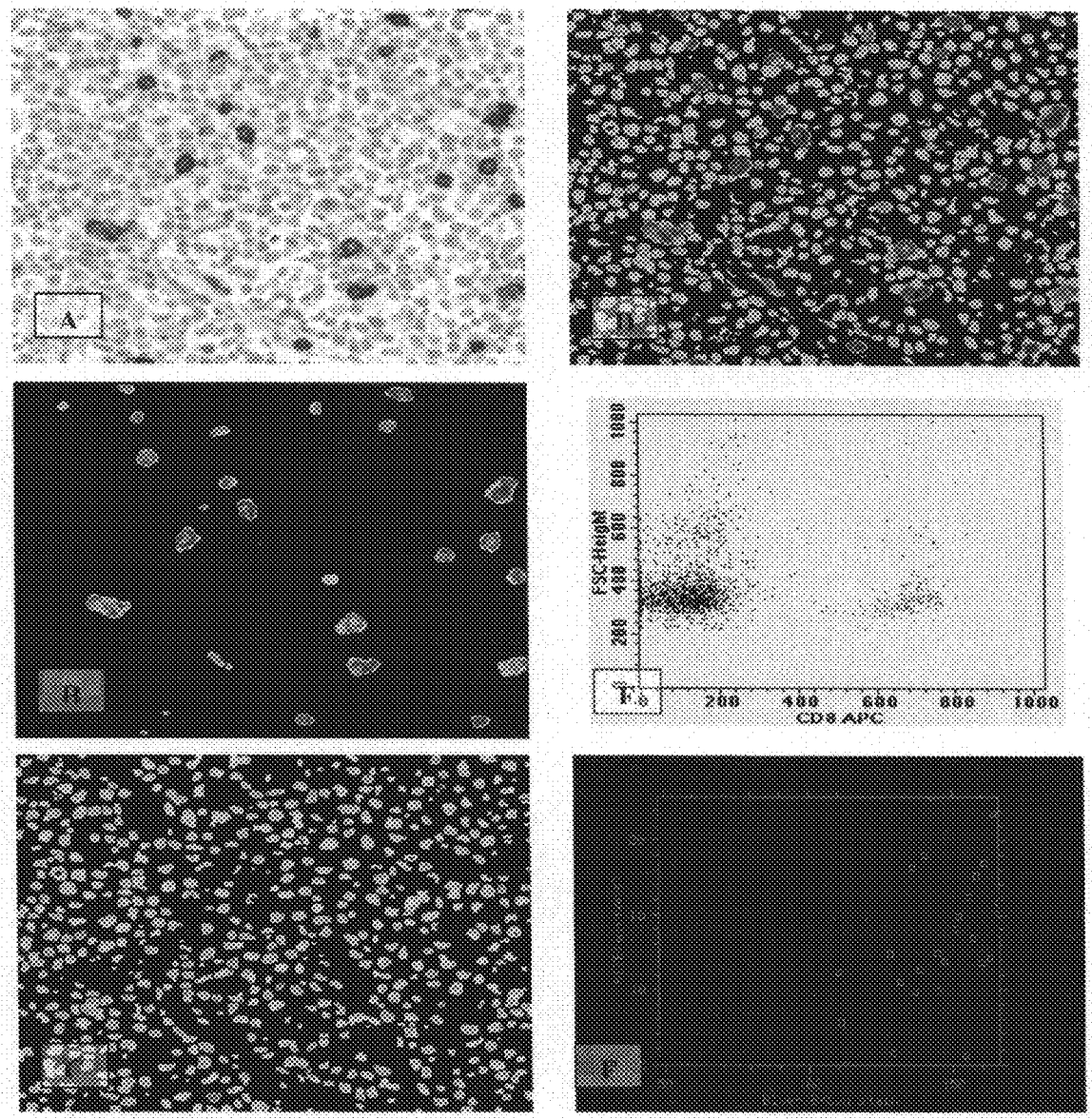
FIG. 7 shows the preferred embodiment with a resulting dot plot histogram results along with a table of exemplary type of image with resulting segmentation into positive and negative cells along with the tabular and dot plot output showing size in microns vs. the staining density and the corresponding flow cytometry results is also shown.

The final result of obtaining the numerator and denominator in FIG. 6 is a set of population statistic, an example of a series of frames on a sample are shown in the image sequence and data FIG. 7.

At the final stage, a preferred embodiment is to display original and intermediate images as well as the final results. The final exemplary images and the resulting two dimensional histogram are shown in FIG. 7 A-D. The original color image A, the intermediate images of single cells belonging to positive cells B and negative cells C are depicted along with the total cells D. The resulting size in microns in Y and staining density in X are shown F along with the same specimen processed as the corresponding flow cytometry results of size vs. complexity E, respectively. The tabular result of the analysis G is also shown.

FIG. 8 is the flow chart of the algorithm detailing the preferred aspect of the novel single cell method. The process is readily applied using a high level language such as JAVA or Visual Basic and use of image processing libraries to accomplish the aims of the invention. FIG. 8a to d is the preferred sequence. We have successfully implemented this flow chart using two high level languages—JAVA and TCL image, to verify that a person ordinarily skilled in the art will be able to convert these algorithm to the computerized system and accomplish the aims laid down. Using a PC with 1.5 gigahertz Intel CPU and JAVA compiled core program, the speed of analysis is between 2 to 3 seconds from image processing of a 512×474 JPEG 24 bit RGB file to all intermediate images and a dot plot display.

CONCLUSION

The invention provides an automated method of single cell image analysis which determines cell population statistic, in a greatly improved manner over manual scoring techniques and new and improved method over prior art in this field. By combining the scientific advantages of automation and the described method, as well as the greatly increased speed with which population can be evaluated, the invention is a major improvement over methods currently available.

The operator is provided with an option to configure the system to perform any or all of these steps and whether to perform certain steps more than once or several times in a row. The sequence of steps can be varied and thereby optimized for specific reagents or reagent combinations; however, the sequence described herein is preferred. An automated image analysis system identifies blue objects of the appropriate size and shape for target nucleus, i.e., lymphocytes, among the blue objects, allowing the imaging system to identify and enumerate all the blue and brown stained cells. In broader application of this invention, other cells are analyzed including large tumor cells, nuclear stained cells, and dual color immunostained cells which could be extensible to several different color chromogen of whatever size target cells.

Computer Implementation

Components of the invention may be realized in hardware or software, or a combination of both. However, preferably, the algorithms and methods of the invention are implemented in one or more processor programs executing on programmable computers each comprising at least one processor of either Intel or Motorola type, at least one data storage system (including volatile and non-volatile memory and/or storage elements), at least one input device, and at least one output device. Program code(s) applied to input data may perform the functions described herein to generate desired output information. The output information is applied to one or more output devices, in known fashion but preferably either an Excel compatible format or a graphics plot showing the distribution of cells based on size vs. the chromogen or dye density. Each program may be implemented in any desired computer language preferably with high level image processing functions (including machine, assembly, high level procedural, or object oriented programming languages) to communicate with a computer system. In any case, the language may be a compiled or interpreted language or both. Each such computer program is preferably stored on a storage media or device (e.g., ROM, CD-ROM, DVD, tape, or magnetic diskette) readable by a general or special purpose programmable computer, for configuring and operating the computer when the storage media or device is read by the computer to perform the procedures described herein. The inventive system may also be considered to be realized as a computer-readable storage medium, or via an internet server medium and hardware configured with connectivity and said computer program, where the storage medium so configured causes a computer to operate in a specific and predefined manner to perform the functions described herein.

ADDITIONAL EMBODIMENTS

There are a plurality of embodiments including a provision for three or more modules to include immunohistochemistry with nuclear reactivity, membrane-cytoplasmic, small, large cell, medium size cells, polar golgi, granular staining, spindle shaped staining, global stromal pattern and others. Another embodiment is to display not size but other nuclear characteristics such as shape, texture, ferret diameter, contour, vs. intensity or vs. detected intranuclear moieties such as chromogenic or in situ hybridization signals.

Another preferred embodiment is the capability of the apparatus and method to be used in ordinary daily pathology practice setting where the diagnostic process of tissue biopsy is the priority. In this mode, the user has little time fiddling with controls of the system and therefore require a robust accommodating mode. In this embodiment, the system is made to dynamically accommodate a wide variation of microscope transmitted light intensity from 4.0 to 6.6 variable rheostat setting (0-10 range).

Another preferred embodiment is the capability of the invention to accommodate a variable immunohistochemical slide product performed by different automated immunohistochemistry machines.

Another preferred embodiment is the capability of the invention to accommodate variable color substrates and dual or triple combinations, both as indicia marker or nuclear counter stain, to include not only brown and blue but a combination of red, orange, black, violet, and any other dark color with a lighter hue of any colored nuclear counter stain.

In one embodiment, examined for speed, a segmentation of a 512×474 RGB image and display of statistical results table or plot data result in a 12-15 seconds using a 100 MHz PowerPC CPU or faster in a Intel Celeron PC 1.4 GHZ using JAVA executed the method in 2-3 seconds.

The invention may be embodied in other forms than those specifically disclosed herein without departing from its spirit or essential characteristics. The described embodiments are to be considered in all respects as illustrative and not restrictive. The scope of the invention is commensurate with the appended claims and all equivalents rather than the foregoing description.

What is claimed is:

1. A tissue cytometry method for analyzing cells in tissue section comprising:
performing light microscopic image analysis on paraffin embedded tissue section comprising:
collecting light scattered by cells with an apparatus comprising:
an optical microscope with image magnifying means and scanning means; said scanning means comprising:
a 3-channel RGB CCD camera;
a static glass slide with tissue and calibrator section stained by immunohistochemistry means;
a brightfield transmitted illumination means for providing a beam of light directed at cells in said tissue section;
a programmed personal computer that:
captures a digital image from said tissue section;
stores said digital image; and
analyzes said digital image,
Multi-stage thresholding and morphologic processing of said digital image comprising the steps of:
separating from said digital image of red, green, and blue channels the respective image planes containing gray-scale values of each channel contained in said digital image;
applying dynamic thresholding to said gray-scale image planes to yield thresholded masks corresponding to red, green, and blue channels, respectively;
combining said masks for red and blue planes using a logical OR operation to create a combined mask;
masking said digital image with the said combined mask to get a raw working image color herein named preliminary raw working image;
further analyzing said preliminary raw working image to get immunostained cells comprising the steps:
calculating epsilon fraction as quotient of blue channel gray-scale image plane of preliminary raw working image divided by brightness channel of preliminary raw working image;
separating said digital image into hue, saturation, and brightness channels representing the respective hue, saturation and brightness values contained in said digital image;
applying entropy thresholding to said hue channel masked by said preliminary raw working image mask to create an entropy-thresholded secondary raw working image mask;
creating a tertiary raw working image mask by applying a logical XOR operation to said entropy-thresholded secondary raw working image mask and said preliminary raw working image mask;
masking said brightness channel with said tertiary raw working image mask to create a quaternary raw working image;
applying isodata thresholding to said quaternary raw working image mask to create an isodata-thresholded quaternary image mask;
combining said isodata-thresholded quaternary image mask and said isodata-thresholded secondary raw working image mask using a logical OR operation to create a quinary raw working image mask;
masking said blue entropy-thresholded channel with said quinary raw working image mask to create a senary raw working image;
applying entropy thresholding using epsilon fraction parameter to said senary raw working image to create an entropy-thresholded senary raw working image mask;
combining said senary raw working image and said quinary raw working image using a logical XOR operation to create an immunostained objects image mask and masking said digital image to create an immunostained objects image;
applying said morphological processing to said immunostained objects image mask to create a morphological immunostained objects image mask;
applying watershed processing to said morphological immunostained objects image mask to create a watershed immunostained objects image mask;
applying said morphological processing to said watershed immunostained objects image mask to create a final immunostained objects image mask representing immunostained cell mask;
masking said digital image with said final immunostained objects image mask to create a final immunostained objects image representing immunostained cells;
inverting said immunostained objects image mask to create an inverted immunostained objects image mask and masking said digital image to create an inverted immunostained objects image;
applying isodata thresholding to red channel within said inverted immunostained objects image to create a primary non-immunostained cell object image mask;
combining said quinary raw working image with said primary non-immunostained cell object image mask in logical OR to create a secondary non-immunostained cell object image and a secondary non-immunostained cell object image mask, respectively;
applying isodata thresholding to blue channel within secondary non-immunostained cell object image to create an tertiary non-immunostained cell object image mask;
combining said tertiary non-immunostained cell object image mask with said inverted immunostained objects image mask in logical OR and with said secondary non-immunostained cell object image mask in logical AND to create a quaternary non-immunostained objects image mask;
applying morphological processing to said tertiary non-immunostained objects image mask to create a morphological quaternary non-immunostained objects image mask;
applying watershed processing to said non-immunostained objects image to create a watershed quaternary non-immunostained objects image mask;
applying morphological processing to said watershed quaternary non-immunostained objects image mask to create a final non-immunostained objects image mask and masking said digital image to create a final non-immunostained objects image representing non-immunostained cells;
assigning final immunostained objects and final non-immunostained objects as final positive cell objects and final negative cell objects, respectively.

2. The method of claim 1 further comprising:
applying declumping processing comprising the steps of:
separating said digital image into immunostained and non-immunostained cells;
applying morphologic processing to clumps of unseparated said final positive cell objects and said final negative cell objects;
separating clumps of said cell objects into single cell objects representing single cells;
analyzing said single immunostained cells and non-immunostained cells for a plurality of cell characteristics including at least cell size and the corresponding cell staining density per cell;
converting cell size to cell nuclear diameter;
comparing cell nuclear diameter to predefined diameter of said cell type of a defined class;
reassigning cell objects with diameter beyond the limit of a defined cell type of a defined class to clumps of unseparated cells;
applying declumping processing to get separated clumps of said cell objects into single cell objects representing single cells.

3. The method of claim 1 wherein said steps of analyzing said digital image further comprises:
applying isodata thresholding to said red channel masked by said preliminary raw working image mask to create an isodata-thresholded secondary raw working image mask;
creating a second tertiary raw working image mask by applying a logical XOR operation to said isodata-thresholded secondary raw working image mask and said preliminary raw working image mask;
masking said brightness channel with said second tertiary raw working image mask to create a second quaternary raw working image;
applying isodata thresholding to said second quaternary raw working image mask to create an second isodata-thresholded quaternary image mask;
combining said second isodata-thresholded quaternary image mask and said isodata-thresholded secondary raw working image mask using a logical OR operation to create a second quinary raw working image mask;
masking said blue entropy-thresholded channel with said second quinary raw working image mask to create a second senary raw working image;
applying entropy thresholding to said second senary raw working image to create second entropy-thresholded senary raw working image mask;
combining said second senary raw working image and said second quinary raw working image using a logical XOR operation to create a second immunostained objects image mask and masking said digital image to create an second immunostained objects image;
applying said morphological processing to said second immunostained objects image mask to create a second morphological immunostained objects image mask;
applying watershed processing to said second morphological immunostained objects image mask to create a second watershed immunostained objects image mask;
applying said morphological processing to said second watershed immunostained objects image mask to create a second final immunostained objects image mask representing second immunostained cell mask;
masking said digital image with said second final immunostained objects image mask to create a second final immunostained objects image representing second immunostained cells;
inverting said second immunostained objects image mask to create a second inverted immunostained objects image mask and masking said digital image to create an second inverted immunostained objects image;
applying isodata thresholding to red channel within said second inverted immunostained objects image to create a second primary non-immunostained cell object image mask;
combining said second quinary raw working image with said primary non-immunostained cell object image mask in logical OR to create a second secondary non-immunostained cell object image and a second secondary non-immunostained cell object image mask, respectively;
applying isodata thresholding to blue channel within second secondary non-immunostained cell object image to create an second tertiary non-immunostained cell object image mask;
combining said second tertiary non-immunostained cell object image mask with said second inverted immunostained objects image mask in logical OR and with said second secondary non-immunostained cell object image mask in logical AND to create a second quaternary non-immunostained objects image mask;
applying morphological processing to said second tertiary non-immunostained objects image mask to create a second morphological quaternary non-immunostained objects image mask;
applying watershed processing to said second non-immunostained objects image to create a second watershed quaternary non-immunostained objects image mask;
applying morphological processing to said second watershed quaternary non-immunostained objects image mask to create a second final non-immunostained objects image mask and masking said digital image to create a second final non-immunostained objects image representing second non-immunostained cells;
assigning final immunostained objects and final non-immunostained objects based on thresholding red channel, second images and image masks as final positive cell objects and final negative cell objects, respectively.

* * * * *